US008173595B2

(12) United States Patent
Dai et al.

(10) Patent No.: US 8,173,595 B2
(45) Date of Patent: May 8, 2012

(54) METHODS AND COMPOSITIONS FOR THE INHIBITION OF THROMBUS FORMATION

(75) Inventors: Kesheng Dai, Chicago, IL (US); Xiaoping Du, Westmont, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 1130 days.

(21) Appl. No.: 11/579,291

(22) PCT Filed: Apr. 27, 2005

(86) PCT No.: PCT/US2005/014528
§ 371 (c)(1),
(2), (4) Date: Jan. 2, 2008

(87) PCT Pub. No.: WO2005/110494
PCT Pub. Date: Nov. 24, 2005

(65) Prior Publication Data
US 2008/0293628 A1 Nov. 27, 2008

Related U.S. Application Data

(60) Provisional application No. 60/568,042, filed on May 4, 2004.

(51) Int. Cl.
*A61K 38/16* (2006.01)
(52) U.S. Cl. ...................... 514/12.2; 435/375
(58) Field of Classification Search .................. None
See application file for complete search history.

(56) References Cited

U.S. PATENT DOCUMENTS
6,177,059 B1 * 1/2001 Matsuda et al. ............. 424/1.21

OTHER PUBLICATIONS

Bodnar et al., J. of Bio. Chem., 1999, vol. 274, No. 47, pp. 33474-33479.*
Andrews et al.; "Binding of Purified 14-3-3ξ Signaling Protein to Discrete Amino Acid Sequences within the Cytoplasmic Domain of the Platelet Membrane Glycoprotein Ib-IX-V Complex," *Biochemistry*, 37:638-647 (1998).
Andrews et al.; "Identification of a Region in the Cytoplasmic Domain of the Platelet Membrane Glycoprotein Ib-IX Complex That Binds to Purified Actin-binding Protein," *J. Biol. Chem.*, 267(26):18605-18611 (1992).
Berndt et al.; "Purification and preliminary characterization of the glycoprotein Ib complex in the human platelet membrane," Eur. J. Biochem., 151(3):637-649 (1985).
Berson, Solomon A., et al.; "State of Human Growth Hormone in Plasma and Changes in Stored Solutions of Pituitary Growth Hormone," *J. Biol. Chem.*, 241(24):5745-5749 (1966).
Bodnar et al.; "Regulation of Glycoprotein Ib-IX-von Willebrand Factor Interaction by cAMP-dependent Protein Kinase-mediated Phosphorylation at Ser$^{166}$ of Glycoprotein Ibβ," *J. Biol. Chem.*, 277(49):47080-47087 (2002).
Bodnar et al.; "The Cytoplasmic Domain of the Platelet Glycoprotein Ibα Is Phosphorylated at Serine 609," *J.Biol.Chem.*, 274:33474-33479 (1999).
Braselmann et al.; "BCR and RAF form a complex in vivo via 14-3-3 Proteins," *EMBO J.* 14(19):4839-4848 (1995).
Calverley et al.; "Human Signaling Protein 14-3-3ζ Interacts With Platelet Glycoprotein Ib Subunits Ibα and Ibβ," *Blood*, 91:1295-1303 (1998).
Coller, Barry S.; "Inhibition of von Willebrand Factor-Dependent Platelet Function by Increased Platelet Cyclic AMP and Its Prevention by Cytoskeleton-Disrupting Agents," *Blood*, 57:846-855 (1981).
Du et al.; "Association of a Phospholipase $A_2$ (14-3-3 Protein) with the Platelet Glycoprotein Ib-IX Complex," *J. Biol. Chem.*, 269:8287-18290 (1994).
Du et al.; "Identification of a Binding Sequence for the 14-3-3 Protein within the Cytoplasmic Domain of the Adhesion Receptor, Platelet Glycoprotein Ibα," *J. Biol. Chem.*, 271:7362-7367 (1996).
Englund et al.; "Regulation of von Willebrand Factor Binding to the Platelet Glycoprotein Ib-IX by a Membrane Skeleton-dependent Inside-out Signal," *J. Biol. Chem.*, 276:16952-16959 (2001).
Feng et al.; "Cytoplasmic domains of GpIbα and GpIbβ regulate 14-3-3ζ binding to GpIb/IX/V," *Blood*, 95(2):551-557 (2000).
Feng et al.; "Filamin a binding to the cytoplasmic tail of glycoprotein Ibα regulates on Willebrand factor-induced platelet activation," *Blood*, 102(6):2122-2129 (2003).
Fox et al.; "Cyclic AMP-dependent Phosphorylation of Glycoprotein Ib Inhibits Collagen-induced Polymerization of Actin in Platelets," *J. Biol. Chem.*, 264(16):9520-9526 (1989).
Fox et al.; "Identification of Glycoprotein Ibβ as One of the Major Proteins Phosphorylated during Exposure of Intact Platelets to Agents That Activate cyclic AMP-dependent Protein Kinase," *J. Biol. Chem.*, 262(26):12627-12631 (1987).
Fu et al.; "14-3-3 Proteins: Structure, Function, and Regulation," *Annu. Rev. Pharmacol. Toxicol.*, 40:617-647 (2000).
Gu et al.; "A Novel Ligand-binding Site in the ζ-Form 14-3-3 Protein Recognizing the Platelet Glycoprotein Ibα and Distinct from the c-Raf-binding Site," *J. Biol. Chem.*, 273:33465-33471 (1998).
International Search Report for PCT/US2005/14528; mailed Apr. 19, 2006.
Li et al.; "A Stimulatory Role for cGMP-Dependent Protein Kinase in Platelet Activation," *Cell*, 112:77-86 (2003).
Liu et al.; "Crystal sructure of the zeta isoform of the 14-3-3 protein," *Nature*, 376:191-194 (1995).
Lopez et al.; "Cloning of the α chain of human platelet glycoprotein Ib: A transmembrane protein with homology to leucine-rich $α_2$-glycoprotein," *Proc. Natl. Acad. Sci. USA*, 84(16):5615-5619 (1987).
Lopez et al.; "The α and β chains of human platelet glycoprotein Ib are both transmembrane proteins containing a leucine-rich amino acid sequence," *Proc. Natl. Acad. Sci. USA*, 85(7):2135-2139 (1988).
Moake, Joel L.; "Thrombotic Thrombocytopenic Purpura: The Systematic Clumping 'Plague'," *Annu. Rev. Med.*, 53:75-88 (2002).

(Continued)

*Primary Examiner* — Christopher R. Tate
*Assistant Examiner* — Roy Teller
(74) *Attorney, Agent, or Firm* — Marshall, Gerstein & Borun LLP

(57) ABSTRACT

The present invention is directed to anti-platelet peptides that may be used in various methods for the treatment or prophylaxis of thrombosis. More specifically, the specification describes methods and compositions for making and using compositions GPIbα fragments as anti-platelet agents. The present invention is also directed to peptides that inhibit intracellular function of 14-3-3.

12 Claims, 5 Drawing Sheets

OTHER PUBLICATIONS

Figures 1A, 1B, 1C, 1D, 1E:
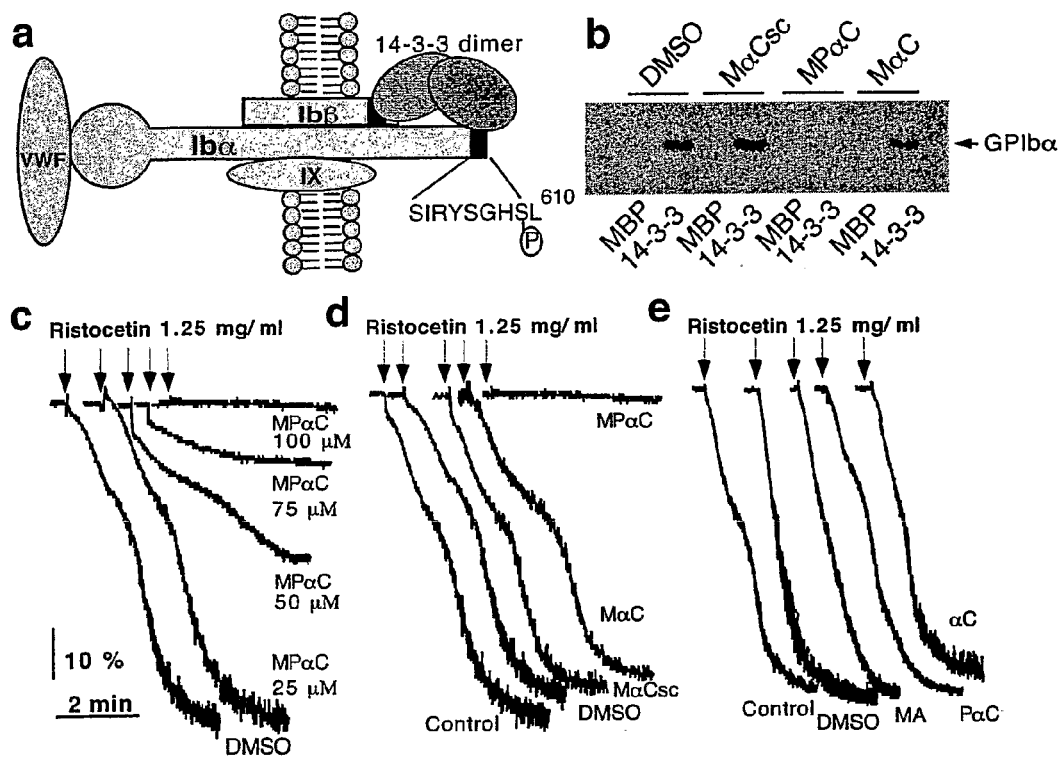

Offermanns et al.; "Defective platelet activation in $G\alpha_q$-deficient mice," *Nature*, 389:183-186 (1997).

Ruan et al.; "A Murine Antiglycoprotein Ib Complex Monoclonal Antibody, SZ 2, Inhibits Platelet Aggregation Induced by Both Ristocetin and Collagen," *Blood*, 69(2):570-577 (1987).

Ruan et al.; "Von Willebrand Factor (VWF)," *Chung Hua Nei Ko Tsa Chih*, 25(9):547-550, 576, (1986).

Ruggeri, Zaverio M.; "The Platelet Glycoprotein Ib-IX Complex," *Prog Hemost Thromb*, 10:35-68 (1991).

Sambrano et al.; "Role of thormbin signalling in platelets in haemostasis and thrombosis," *Nature*, 413:74-78 (2001).

Slack et al.; "Flow Chambers and their Standardization for Use in Studies of Thrombosis," *Thromb. Haemost.*, 72(5):777-781 (1994).

Wardell et al.; "Platelet Glycoprotein $Ib_\beta$ Is Phosphorylated on Serine 166 by Cyclic AMP-dependent Protein Kinase," *J. Biol. Chem.*, 264:15656-15661 (1989).

Ware, J.; "Molecular Analyses of the Platelet Glycoprotein Ib-IX-V Receptor," *Thromb Haemost* 79, 466-478, 1998).

Ware, Jerry, et al.; "Generation and rescue of a muring model of platelet dysfunction: The Bernard-Soulier syndrome," *Proc. Natl. Acad, Sci. USA*, 97(6):2803-2808 (2000).

Xiao et al.; "Structure of a 14-3-3 protein and implications for coordination of multiple signalling pathways," *Nature*, 376(6536):188-191 (1995).

\* cited by examiner

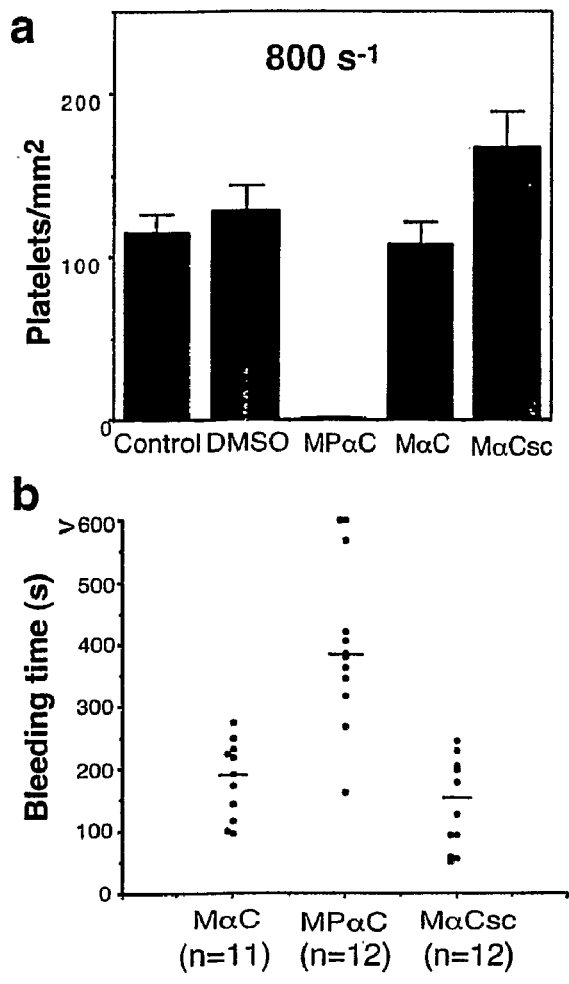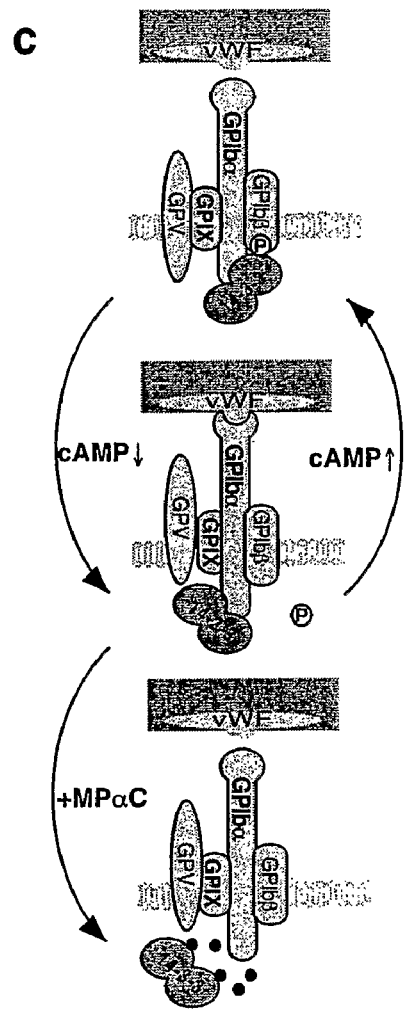
Figures 4A – 4C

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa = Serine derivatized with a myristoyl group
<220> FEATURE:
<221> NAME/KEY: misc_feature
<222> LOCATION: (8)..(8)
<223> OTHER INFORMATION: Serine at position 8 is phosphorylated

<400> SEQUENCE: 1

Xaa Ile Arg Tyr Ser Gly His Ser Leu
1               5

<210> SEQ ID NO 2
<211> LENGTH: 2480
<212> TYPE: DNA
<213> ORGANISM: Homo sapiens

<400> SEQUENCE: 2
gacgctctgt gccttcggag gtctttctgc ctgcctgtcc tcatgcctct cctcctcttg      60
```

-continued

```
ctgctcctgc tgccaagccc cttacacccc caccccatct gtgaggtctc caaagtggcc      120
agccacctag aagtgaactg tgacaagagg aatctgacag cgctgcctcc agacctgccg      180
aaagacacaa ccatcctcca cctgagtgag aacctcctgt acaccttctc cctggcaacc      240
ctgatgcctt acactcgcct cactcagctg aacctagata ggtgcgagct caccaagctc      300
caggtcgatg ggacgctgcc agtgctgggg accctggatc tatcccacaa tcagctgcaa      360
agcctgccct tgctagggca gacactgcct gctctcaccg tcctggacgt ctccttcaac      420
cggctgacct cgctgcctct tggtgccctg cgtggtcttg gcgaactcca gagctctac       480 ctgaaaggca atgagctgaa gaccctgccc cagggctcc tgacgcccac acccaagctg       540
gagaagctca gtctggctaa caacaacttg actgagctcc ccgctgggct cctgaatggg      600
ctggagaatc tcgacaccct tctcctccaa gagaactcgc tgtatacaat accaaagggc      660
ttttttgggt cccacctcct gccttttgct tttctccacg ggaacccctg gttatgcaac      720
tgtgagatcc tctatttccg tcgctggctg caggacaatg ctgaaaatgt ctacgtatgg      780
aagcaaggtg tggacgtcaa ggccatgacc tctaacgtgg ccagtgtgca gtgtgacaat      840
tcagacaagt ttcccgtcta caaataccca ggaaagggt gccccaccct tggtgatgaa       900
ggtgacacag acctatatga ttactaccca gaagaggaca ctgagggcga taaggtgcgt      960
gccacaagga ctgtggtcaa gttccccacc aaagccccata caaccccctg gggtctattc     1020
tactcatggt ccactgcttc tctagacagc caaatgccct cctccttgca tccaacacaa      1080
gaatccacta aggagcagac cacattccca cctagatgga ccccaaattt cacacttcac      1140
atggaatcca tcacattctc caaaactcca aaatccacta ctgaaccaac cccaagcccg      1200
accacctcag agcccgtccc ggagcccgcc caaacatga ccaccctgga gcccactcca       1260
agcccgacca ccccagagcc cacctcagag cccgcccca gccgaccac cccggagccc        1320 accccaatcc cgaccatcgc cacaagcccg accatcctgg tgtctgccac aagcctgatc      1380
actccaaaaa gcacattttt aactaccaca aaacccgtat cactcttaga atccaccaaa     1440
aaaaccatcc ctgaacttga tcagccacca aagctccgtg gggtgctcca agggcatttg     1500
gagagctcca gaaatgaccc ttttctccac cccgactttt gctgcctcct cccctgggc     1560 ttctatgtct tgggtctctt ctggctgctc tttgcctctg tggtcctcat cctgctgctg     1620
agctgggttg ggcatgtgaa accacaggcc ctggactctg ccaaggtgc tgctctgacc      1680 acagccacac aaaccacaca cctggagctg cagaggggac ggcaagtgac agtgccccgg     1740
gcctggctgc tcttccttcg aggttcgctt cccactttcc gctccagcct cttcctgtgg     1800
gtacggccta atggccgtgt ggggcctcta gtggcaggaa ggaggccctc agctctgagt     1860
cagggtcgtg gtcaggacct gctgagcaca gtgagcatta ggtactctgg ccacagcctc     1920
tgagggtggg aggtttgggg accttgagag aagagcctgt gggctctcct attggaatct    1980
agttgggggt tggaggggta aggaacacag ggtgataggg gaggggtctt agttcctttt     2040
tctgtatcag aagccctgtc ttcacaacac aggcacacaa tttcagtccc agccaaagca    2100 gaagggtaa tgcatggac ttggcggggg gacaagacaa agctcccgat gctgcatggg      2160
gcgctgccag atctcacggt gaaccatttt ggcagaatac agcatggttc ccacatgcat    2220
ttatgcacag aagaaaatct ggaaagtgat ttatcaggat gtgagcactc gttgtgtctg    2280
gatgttacaa atatgggtgg ttttattttc ttttttccctg tttagcattt tctagttttc   2340
ttatcaggat gtgagcactc gttgtgtctg gatgttacaa atatgggtgg ttttattttc    2400
tttttccctg tttagcattt tctagttttc cactattatt gtatattatc tgtataataa    2460
```
aaaataattt tagggttggg                                                      2480

<210> SEQ ID NO 3
<211> LENGTH: 626
<212> TYPE: PRT
<213> ORGANISM: Homo sapiens

<400> SEQUENCE: 3

```
Met Pro Leu Leu Leu Leu Leu Leu Pro Ser Pro Leu His Pro
1               5                   10                  15

His Pro Ile Cys Glu Val Ser Lys Val Ala Ser His Leu Glu Val Asn
            20                  25                  30

Cys Asp Lys Arg Asn Leu Thr Ala Leu Pro Pro Asp Leu Pro Lys Asp
        35                  40                  45

Thr Thr Ile Leu His Leu Ser Glu Asn Leu Leu Tyr Thr Phe Ser Leu
    50                  55                  60

Ala Thr Leu Met Pro Tyr Thr Arg Leu Thr Gln Leu Asn Leu Asp Arg
65                  70                  75                  80

Cys Glu Leu Thr Lys Leu Gln Val Asp Gly Thr Leu Pro Val Leu Gly
                85                  90                  95

Thr Leu Asp Leu Ser His Asn Gln Leu Gln Ser Leu Pro Leu Leu Gly
            100                 105                 110

Gln Thr Leu Pro Ala Leu Thr Val Leu Asp Val Ser Phe Asn Arg Leu
        115                 120                 125

Thr Ser Leu Pro Leu Gly Ala Leu Arg Gly Leu Gly Glu Leu Gln Glu
    130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175

Thr Glu Leu Pro Ala Gly Leu Leu Asn Gly Leu Glu Asn Leu Asp Thr
            180                 185                 190

Leu Leu Leu Gln Glu Asn Ser Leu Tyr Thr Ile Pro Lys Gly Phe Phe
        195                 200                 205

Gly Ser His Leu Leu Pro Phe Ala Phe Leu His Gly Asn Pro Trp Leu
    210                 215                 220

Cys Asn Cys Glu Ile Leu Tyr Phe Arg Arg Trp Leu Gln Asp Asn Ala
225                 230                 235                 240

Glu Asn Val Tyr Val Trp Lys Gln Gly Val Asp Val Lys Ala Met Thr
                245                 250                 255

Ser Asn Val Ala Ser Val Gln Cys Asp Asn Ser Asp Lys Phe Pro Val
            260                 265                 270

Tyr Lys Tyr Pro Gly Lys Gly Cys Pro Thr Leu Gly Asp Glu Gly Asp
        275                 280                 285

Thr Asp Leu Tyr Asp Tyr Tyr Pro Glu Glu Asp Thr Glu Gly Asp Lys
    290                 295                 300

Val Arg Ala Thr Arg Thr Val Val Lys Phe Pro Thr Lys Ala His Thr
305                 310                 315                 320

Thr Pro Trp Gly Leu Phe Tyr Ser Trp Ser Thr Ala Ser Leu Asp Ser
                325                 330                 335

Gln Met Pro Ser Ser Leu His Pro Thr Gln Glu Ser Thr Lys Glu Gln
            340                 345                 350

Thr Thr Phe Pro Pro Arg Trp Thr Pro Asn Phe Thr Leu His Met Glu
        355                 360                 365

Ser Ile Thr Phe Ser Lys Thr Pro Lys Ser Thr Thr Glu Pro Thr Pro
```

```
                370                 375                 380
Ser Pro Thr Thr Ser Glu Pro Val Pro Glu Pro Ala Pro Asn Met Thr
385                 390                 395                 400

Thr Leu Glu Pro Thr Pro Ser Pro Thr Thr Pro Glu Pro Thr Ser Glu
                405                 410                 415

Pro Ala Pro Ser Pro Thr Thr Pro Glu Pro Thr Pro Ile Pro Thr Ile
                420                 425                 430

Ala Thr Ser Pro Thr Ile Leu Val Ser Ala Thr Ser Leu Ile Thr Pro
                435                 440                 445

Lys Ser Thr Phe Leu Thr Thr Thr Lys Pro Val Ser Leu Leu Glu Ser
        450                 455                 460

Thr Lys Lys Thr Ile Pro Glu Leu Asp Gln Pro Pro Lys Leu Arg Gly
465                 470                 475                 480

Val Leu Gln Gly His Leu Glu Ser Ser Arg Asn Asp Pro Phe Leu His
                485                 490                 495

Pro Asp Phe Cys Cys Leu Leu Pro Leu Gly Phe Tyr Val Leu Gly Leu
                500                 505                 510

Phe Trp Leu Leu Phe Ala Ser Val Val Leu Ile Leu Leu Leu Ser Trp
        515                 520                 525

Val Gly His Val Lys Pro Gln Ala Leu Asp Ser Gly Gln Gly Ala Ala
530                 535                 540

Leu Thr Thr Ala Thr Gln Thr Thr His Leu Glu Leu Gln Arg Gly Arg
545                 550                 555                 560

Gln Val Thr Val Pro Arg Ala Trp Leu Leu Phe Leu Arg Gly Ser Leu
                565                 570                 575

Pro Thr Phe Arg Ser Ser Leu Phe Leu Trp Val Arg Pro Asn Gly Arg
                580                 585                 590

Val Gly Pro Leu Val Ala Gly Arg Arg Pro Ser Ala Leu Ser Gln Gly
                595                 600                 605

Arg Gly Gln Asp Leu Leu Ser Thr Val Ser Ile Arg Tyr Ser Gly His
        610                 615                 620

Ser Leu
625

<210> SEQ ID NO 4
<211> LENGTH: 610
<212> TYPE: PRT
<213> ORGANISM: Homo sapiens

<400> SEQUENCE: 4

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
        50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
```

```
                    115                 120                 125
Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                    165                 170                 175

Leu Leu Leu Gln Glu Asn Ser Leu Tyr Thr Ile Pro Lys Gly Phe Phe
                180                 185                 190

Gly Ser His Leu Leu Pro Phe Ala Phe Leu His Gly Asn Pro Trp Leu
                    195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                    245                 250                 255

Tyr Lys Tyr Pro Gly Lys Gly Cys Pro Thr Leu Gly Asp Glu Gly Asp
                260                 265                 270

Thr Asp Leu Tyr Asp Tyr Tyr Pro Glu Glu Asp Thr Glu Gly Asp Lys
                    275                 280                 285

Val Arg Ala Thr Arg Thr Val Lys Phe Pro Thr Lys Ala His Thr
                    290                 295                 300

Thr Pro Trp Gly Leu Phe Tyr Ser Trp Ser Thr Ala Ser Leu Asp Ser
305                 310                 315                 320

Gln Met Pro Ser Ser Leu His Pro Thr Gln Glu Ser Thr Lys Glu Gln
                    325                 330                 335

Thr Thr Phe Pro Pro Arg Trp Thr Pro Asn Phe Thr Leu His Met Glu
                340                 345                 350

Ser Ile Thr Phe Ser Lys Thr Pro Lys Ser Thr Glu Pro Thr Pro
                355                 360                 365

Ser Pro Thr Thr Ser Glu Pro Val Pro Glu Pro Ala Pro Asn Met Thr
370                 375                 380

Thr Leu Glu Pro Thr Pro Ser Pro Thr Thr Pro Glu Pro Thr Ser Glu
385                 390                 395                 400

Pro Ala Pro Ser Pro Thr Thr Pro Glu Pro Thr Ile Pro Thr Ile
                    405                 410                 415

Ala Thr Ser Pro Thr Ile Leu Val Ser Ala Thr Ser Leu Ile Thr Pro
                420                 425                 430

Lys Ser Thr Phe Leu Thr Thr Thr Lys Pro Val Ser Leu Leu Glu Ser
                435                 440                 445

Thr Lys Lys Thr Ile Pro Glu Leu Asp Gln Pro Pro Lys Leu Arg Gly
450                 455                 460

Val Leu Gln Gly His Leu Glu Ser Ser Arg Asn Asp Pro Phe Leu His
465                 470                 475                 480

Pro Asp Phe Cys Cys Leu Leu Pro Leu Gly Phe Tyr Val Leu Gly Leu
                    485                 490                 495

Phe Trp Leu Leu Phe Ala Ser Val Val Leu Ile Leu Leu Leu Ser Trp
                500                 505                 510

Val Gly His Val Lys Pro Gln Ala Leu Asp Ser Gly Gln Gly Ala Ala
                515                 520                 525

Leu Thr Thr Ala Thr Gln Thr Thr His Leu Glu Leu Gln Arg Gly Arg
530                 535                 540
```

-continued

```
Gln Val Thr Val Pro Arg Ala Trp Leu Leu Phe Leu Arg Gly Ser Leu
545                 550                 555                 560

Pro Thr Phe Arg Ser Ser Leu Phe Leu Trp Val Arg Pro Asn Gly Arg
                565                 570                 575

Val Gly Pro Leu Val Ala Gly Arg Arg Pro Ser Ala Leu Ser Gln Gly
            580                 585                 590

Arg Gly Gln Asp Leu Leu Ser Thr Val Ser Ile Arg Tyr Ser Gly His
        595                 600                 605

Ser Leu
    610
```

<210> SEQ ID NO 5
<211> LENGTH: 25
<212> TYPE: DNA
<213> ORGANISM: Artificial sequence
<220> FEATURE:
<223> OTHER INFORMATION: Synthetic primer

<400> SEQUENCE: 5
agaagaattc gctgctctga ccaca                                        25

<210> SEQ ID NO 6
<211> LENGTH: 30
<212> TYPE: DNA
<213> ORGANISM: Artificial sequence
<220> FEATURE:
<223> OTHER INFORMATION: Synthetic primer

<400> SEQUENCE: 6
taagtctaga tcagagggcg tggccagagt                                   30

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Arg Gly Asp Ser
1

<210> SEQ ID NO 8
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa = Serine derivatized with a myristoyl group

<400> SEQUENCE: 8

Xaa Ile Arg Tyr Ser Gly His Asp Leu
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Ser Ile Arg Tyr Ser Gly His Glu Leu

-continued

```
<210> SEQ ID NO 10
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: The Serine at position 6 is phosphorylated.

<400> SEQUENCE: 10

Arg Tyr Ser Gly His Ser Leu
1               5

<210> SEQ ID NO 11
<211> LENGTH: 100
<212> TYPE: PRT
<213> ORGANISM: Artificial sequence
<220> FEATURE:
<223> OTHER INFORMATION: Synthetic peptide

<400> SEQUENCE: 11

Ser Trp Val Gly His Val Lys Pro Gln Ala Leu Asp Ser Gly Gln Gly
1               5                   10                  15

Ala Ala Leu Thr Thr Ala Thr Gln Thr Thr His Leu Glu Leu Gln Arg
            20                  25                  30

Gly Arg Gln Val Thr Val Pro Arg Ala Trp Leu Leu Phe Leu Arg Gly
        35                  40                  45

Ser Leu Pro Thr Phe Arg Ser Ser Leu Phe Leu Trp Val Arg Pro Asn
    50                  55                  60

Gly Arg Val Gly Pro Leu Val Ala Gly Arg Arg Pro Ser Ala Leu Ser
65                  70                  75                  80

Gln Gly Arg Gly Gln Asp Leu Leu Ser Thr Val Ser Ile Arg Tyr Ser
                85                  90                  95

Gly His Ser Leu
            100

<210> SEQ ID NO 12
<211> LENGTH: 10
<212> TYPE: PRT
<213> ORGANISM: Artificial sequence
<220> FEATURE:
<223> OTHER INFORMATION: Synthetic peptide

<400> SEQUENCE: 12

Val Ser Ile Arg Tyr Ser Gly His Ser Leu
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic peptide

<400> SEQUENCE: 13

Thr Val Ser Ile Arg Tyr Ser Gly His Ser Leu
1               5                   10

<210> SEQ ID NO 14
<211> LENGTH: 12
<212> TYPE: PRT
```

<213> ORGANISM: Artificial sequence
<220> FEATURE:
<223> OTHER INFORMATION: Synthetic peptide

<400> SEQUENCE: 14

```
Ser Thr Val Ser Ile Arg Tyr Ser Gly His Ser Leu
1               5                   10
```

<210> SEQ ID NO 15
<211> LENGTH: 13
<212> TYPE: PRT
<213> ORGANISM: Artificial sequence
<220> FEATURE:
<223> OTHER INFORMATION: Synthetic peptide

<400> SEQUENCE: 15

```
Leu Ser Thr Val Ser Ile Arg Tyr Ser Gly His Ser Leu
1               5                   10
```

<210> SEQ ID NO 16
<211> LENGTH: 14
<212> TYPE: PRT
<213> ORGANISM: Artificial sequence
<220> FEATURE:
<223> OTHER INFORMATION: Synthetic peptide

<400> SEQUENCE: 16

```
Leu Leu Ser Thr Val Ser Ile Arg Tyr Ser Gly His Ser Leu
1               5                   10
```

<210> SEQ ID NO 17
<211> LENGTH: 15
<212> TYPE: PRT
<213> ORGANISM: Artificial sequence
<220> FEATURE:
<223> OTHER INFORMATION: Synthetic peptide

<400> SEQUENCE: 17

```
Asp Leu Leu Ser Thr Val Ser Ile Arg Tyr Ser Gly His Ser Leu
1               5                   10                  15
```

<210> SEQ ID NO 18
<211> LENGTH: 16
<212> TYPE: PRT
<213> ORGANISM: Artificial sequence
<220> FEATURE:
<223> OTHER INFORMATION: Synthetic peptide

<400> SEQUENCE: 18

```
Gln Asp Leu Leu Ser Thr Val Ser Ile Arg Tyr Ser Gly His Ser Leu
1               5                   10                  15
```

<210> SEQ ID NO 19
<211> LENGTH: 17
<212> TYPE: PRT
<213> ORGANISM: Artificial sequence
<220> FEATURE:
<223> OTHER INFORMATION: Synthetic peptide

<400> SEQUENCE: 19

```
Gly Gln Asp Leu Leu Ser Thr Val Ser Ile Arg Tyr Ser Gly His Ser
1               5                   10                  15

Leu
```

<210> SEQ ID NO 20
<211> LENGTH: 18
<212> TYPE: PRT

<213> ORGANISM: Artificial sequence
<220> FEATURE:
<223> OTHER INFORMATION: Synthetic peptide

<400> SEQUENCE: 20

Arg Gly Gln Asp Leu Leu Ser Thr Val Ser Ile Arg Tyr Ser Gly His
1               5                   10                  15

Ser Leu

<210> SEQ ID NO 21
<211> LENGTH: 19
<212> TYPE: PRT
<213> ORGANISM: Artificial sequence
<220> FEATURE:
<223> OTHER INFORMATION: Synthetic peptide

<400> SEQUENCE: 21

Gly Arg Gly Gln Asp Leu Leu Ser Thr Val Ser Ile Arg Tyr Ser Gly
1               5                   10                  15

His Ser Leu

<210> SEQ ID NO 22
<211> LENGTH: 20
<212> TYPE: PRT
<213> ORGANISM: Artificial sequence
<220> FEATURE:
<223> OTHER INFORMATION: Synthetic peptide

<400> SEQUENCE: 22

Gln Gly Arg Gly Gln Asp Leu Leu Ser Thr Val Ser Ile Arg Tyr Ser
1               5                   10                  15

Gly His Ser Leu
            20

<210> SEQ ID NO 23
<211> LENGTH: 21
<212> TYPE: PRT
<213> ORGANISM: Artificial sequence
<220> FEATURE:
<223> OTHER INFORMATION: Synthetic peptide

<400> SEQUENCE: 23

Ser Gln Gly Arg Gly Gln Asp Leu Leu Ser Thr Val Ser Ile Arg Tyr
1               5                   10                  15

Ser Gly His Ser Leu
            20

<210> SEQ ID NO 24
<211> LENGTH: 22
<212> TYPE: PRT
<213> ORGANISM: Artificial sequence
<220> FEATURE:
<223> OTHER INFORMATION: Synthetic peptide

<400> SEQUENCE: 24

Leu Ser Gln Gly Arg Gly Gln Asp Leu Leu Ser Thr Val Ser Ile Arg
1               5                   10                  15

Tyr Ser Gly His Ser Leu
            20

<210> SEQ ID NO 25
<211> LENGTH: 23
<212> TYPE: PRT
<213> ORGANISM: Artificial sequence
<220> FEATURE:

```
<223> OTHER INFORMATION: Synthetic peptide

<400> SEQUENCE: 25

Ala Leu Ser Gln Gly Arg Gly Gln Asp Leu Leu Ser Thr Val Ser Ile
1               5                   10                  15

Arg Tyr Ser Gly His Ser Leu
            20

<210> SEQ ID NO 26
<211> LENGTH: 24
<212> TYPE: PRT
<213> ORGANISM: Artificial sequence
<220> FEATURE:
<223> OTHER INFORMATION: Synthetic peptide

<400> SEQUENCE: 26

Ser Ala Leu Ser Gln Gly Arg Gly Gln Asp Leu Leu Ser Thr Val Ser
1               5                   10                  15

Ile Arg Tyr Ser Gly His Ser Leu
            20

<210> SEQ ID NO 27
<211> LENGTH: 25
<212> TYPE: PRT
<213> ORGANISM: Artificial sequence
<220> FEATURE:
<223> OTHER INFORMATION: Synthetic peptide

<400> SEQUENCE: 27

Pro Ser Ala Leu Ser Gln Gly Arg Gly Gln Asp Leu Leu Ser Thr Val
1               5                   10                  15

Ser Ile Arg Tyr Ser Gly His Ser Leu
            20                  25

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Ser Ile Arg Tyr Ser Gly His Ser Leu
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Serine at position 8 is phosphorylated

<400> SEQUENCE: 29

Ser Ile Arg Tyr Ser Gly His Ser Leu
1               5
```

METHODS AND COMPOSITIONS FOR THE INHIBITION OF THROMBUS FORMATION

The present application is filed under 35 U.S.C. §371 as a U.S. national phase application of PCT application no. PCT/US05/14528, which was filed Apr. 27, 2005. The aforementioned PCT application claimed benefit of priority of U.S. Provisional Application No. 60/568,042, which was filed May 4, 2004. The entire text of each of the aforementioned applications is incorporated herein by reference.

There is government support for this invention under National Institutes of Health Grant No. HL62350. The government has certain rights in the invention.

BACKGROUND

1. Field of the Invention

The present invention is generally directed to novel peptide-based compositions. More particularly, the present invention identifies new peptides that may be used to inhibit the binding of a key factor in the coagulation cascade, von Wilebrand factor (VWF) to platelets and to inhibit platelet adhesion and thrombus formation. As such, the present invention is directed to methods and compositions that may be used to inhibit thrombus formation and treat disorders associated with thrombus formation. Also, the new peptide-based compositions identified in the present invention may be used to inhibit the function of a family of intracellular proteins, named 14-3-3.

2. Background of the Related Art

Blood vessels operate under significant shear stresses that are a function of blood flow shear rate. Frequently, there is damage to small blood vessels and capillaries. When these vessels are damaged, hemostasis is triggered to stop the bleeding. Under typical circumstances, such an injury is dealt with through a sequence of events commonly referred to as the "thrombus formation". Thrombus formation is dependent upon platelet adhesion, activation and aggregation and the coagulation cascade that culminates in the conversion of soluble fibrinogen to insoluble fibrin clot. Thrombus formation at site of wound prevents extravasation of blood components. Subsequently, wound healing and clot dissolution occurs and blood vessel integrity and flow is restored. Abnormal thrombus formation that causes obstruction of blood vessels is referred to as "thrombosis".

A key step in the thrombus formation is platelet adhesion. In arteries and capillaries where blood flow shear rate is high, initial platelet adhesion is dependent on the binding of von Willebrand factor (VWF) to its platelet receptor, the glycoprotein (GP) Ib-IX-V complex (GPIb-IX) (Ruggeri, Prog Hemost Thromb 10, 35-68, 1991; Ware, Thromb Haemost 79,466-478, 1998). VWF binding to GPIb-IX mediates initial platelet adhesion to blood vessel wall, induces platelet activation and firm adhesion, leading platelet aggregation and formation of thrombus. Thus, inhibition of VWF binding to GPIb-IX leads to inhibition of thrombus formation.

GPIb-IX consists of four subunits, GPIbα, GPIbβ, GPIX and GPV. Extracellular domain of GPIba contains binding sites for VWF and thrombin. Binding of VWF to GPIb is regulated by cytoplasmic domain of GPIb-IX. A phosphoserine-dependent intracellular signaling molecule, ζ-form of 14-3-3 protein (Fu et al., Annu Rev Pharmacol Toxicol 40, 617-647, 2000), interacts with the cytoplasmic domain of GPIbα (Du et al., J Biol Chem 269, 18287-18290, 1994; Du et al., J Biol Chem 271, 7362-7367, 1996) and this interaction is dependent upon phosphorylation at Serine 609 of GPIbα (Bodnar et al., J. Biol. Chem. 274, 33474-33479, 1999).

14-3-3 is a family of intracellular signaling proteins that specifically recognize intracellular proteins that contains specific serine-phosphorylated 14-3-3 binding motifs. Different 14-3-3 binding proteins may have different sequences. However, these proteins are believed to bind to the same ligand binding pocket in 14-3-3. Thus, binding of one ligand may inhibit binding of a different ligand.

While thrombus formation is an essential mechanism by which unnecessary blood loss is avoided, this system often is dysregulated and leads to the formation of aberrant clots in the vasculature of a mammal. Thrombosis, is the physical condition that manifests when a thrombus is present in the vasculature of an animal. A thrombus (also called clot) is—gel-like or solidified blood formed by polymerized fibrin, platelets, and blood elements trapped by the fibrin-platelet net. While certain authorities imply a difference in the meaning of the terms "blood clot" and "thrombus," these terms are typically employed interchangeably in the art to mean an aggregation as described above and the terms are used interchangeably herein.

The presence of thrombi in blood vessels can result in and/or from pathologies or treatments such as myocardial infarction, unstable angina, atrial fibrillation, stroke, renal damage, percutaneous translumenal coronary angioplasty, athreosclerosis, disseminated intravascular coagulation, sepsis, pulmonary embolism and deep vein thrombosis. Blood clots also are seen on the surfaces of artificial organs, shunts and prostheses such as artificial heart valves that are implanted into an animal. In addition, certain pathological conditions (such as genetic lack of VWF cleaving protease, ADAMT13, causes spontaneous binding of VWF to platelets resulting in formation of microthrombi in blood vessels leading to thrombotic thrombocytopenic purpura and other microangiopathy. In order to combat the deleterious effects of thrombosis, anticoagulants, such as heparin are routinely administered. However, the problem with many existing anticoagulants is that they fail to block platelet adhesion and aggregation, and can lead to uncontrolled bleeding or other complications. Therefore, there is a constant need to identify new and improved anti-thrombotic drugs.

The present invention is directed to new compositions that may be used as antithrombotics and/or anti-platelet agents.

SUMMARY OF THE INVENTION

The present invention is directed to peptide-based compositions derived from platelet GPIba C-terminal residues 602-610 and the like to inhibit VWF binding function of GPIb-IX, VWF-mediated platelet adhesion, platelet activation and aggregation, and in vivo thrombus formation. Thus, such compositions may be developed as a new type of anti-thrombotic agents. In particular, the findings of the present invention are based in part on the discovery that 14-3-3 interaction with GPIb-IX is required for the function of GPIb-IX, and thus any inhibitors of this interaction may be used as inhibitors of GPIb-IX and thus used as anti-thrombotic agents. The compositions described herein can be used as inhibitors of intracellular functions of 14-3-3 in cells and in vivo.

Thus, in specific embodiments, the present invention is directed to a composition comprising a myristoylated peptide having an amino acid sequence of, $C_{13}H_{27}$CONH-SIRYS-GHpSL (SEQ ID NO:1 in which the lower case p before serine represents phosphorylation); a fragment of SEQ ID NO:1 that retains a 14-3-3 binding activity, or a conservative variant SEQ ID NO:1 that retains a 14-3-3 binding activity, wherein the myristoyl group is at the C-terminus, or at the N-terminus of the protein. As indicated in preferred embodiments, the peptide is phosphorylated. Preferably, the phosphorylation is on one or more serine/threonine residues of GPIbα. In preferred embodiments, the phosphorylation is at Serine 609. In still other aspects of the invention, the phosphorylated serine residues indicated above are substituted with an aspartic acid or glutamic acid or other composition to simulate the effect of phosphorylation. An exemplary such derivative is a composition comprising the sequence of $C_{13}H_{27}$CONH-SIRYSGHDL (SEQ ID NO:8). In specific embodiments, the peptide is between about 10 amino acids and about 50 amino acids in length. In other embodiments, the peptide is between about 10 amino acids and about 40 amino acids in length. In preferred embodiments, the contacting a peptide of the invention with platelets, or other type of cells inhibits intracellular function of 14-3-3 to interact with other proteins. In particular aspects, the peptides are used for the inhibition of intracellular function of 14-3-3. Such inhibition may be carried out in vivo or in vitro.

The composition of the present invention is a peptide that inhibits the binding of von Willebrands factor (VWF) to blood platelets, or other cells that express GPIb-IX. In specific embodiments, the peptide inhibits VWF binding to GPIb-IX molecules. In other preferred embodiments, the peptide inhibits VWF binding to platelets. In other embodiments, the peptide inhibits VWF binding to cells expressing GPIb-IX. In particular embodiments, the peptide inhibits GPIb-IX-dependent platelet aggregation.

The peptide compositions of the present invention preferably further comprise a pharmaceutically acceptable carrier, diluent or excipient. In additional embodiments, the compositions of the invention further may comprise an additional agent selected from the group consisting of a fibrinolytic molecule, an anticoagulant and an anti-platelet agent. In particular embodiments, the anticoagulant is selected from the group consisting of a heparin, hirudin or activated protein C. Exemplary fibrinolytic molecules include but are not limited to plasmin or a plasminogen activator. Preferred plasminogen activators include but are not limited to staphylokinase, streptokinase, prourokinase, urokinase, tissue-type plasminogen activator and vampire bat plasminogen activator.

The compositions of the invention may further include a heparin composition. More particularly, the heparin composition is a low molecular weight heparin composition. Low molecular weight heparin compositions are well known to those of skill in the art and include but are not limited to tinzaparin, certoparin, parnaparin, nadroparin, ardeparin, enoxaparin, reviparin, reviparin, dalteparin, and fraxiparin.

The compositions comprising an anti-platelet agent may include an anti-platelet agent selected from the group consisting of ticlopidinem aspirin, clopidrigel or an inhibitor of glycoprotein IIb/IIIa function. Other exemplary anti-platelet agents may be selected from the group consisting of Aggrastat™, Aggrenox™, Agrylin™, Flolan™, Integrilin™, Presantine™, Plavix™, Pletal™ and ReoPro™.

The compositions described herein may be formulated for aerosol, intravenous, oral or topical delivery.

Another aspect of the present invention contemplated method of inhibiting platelet adhesion comprising contacting a sample containing platelets with a composition comprising a peptide derived from GP1bα that binds 14-3-3. In other specific aspects of the invention there is a method of decreasing binding of von Willebrand's factor to platelet cells comprising contacting a biological sample containing said platelet cells with a composition comprising a peptide derived from GP1bα that binds 14-3-3. In preferred embodiments, the contacting is carried out in vivo. In other embodiments, the contacting is carried out in vitro.

The methods described herein may be used as methods of prolonging bleeding time in a mammal comprising administering to said mammal a composition of comprising a peptide derived from GP1bα that binds 14-3-3. In exemplary embodiments, the bleeding is in a patient during surgery.

Also encompassed by the present invention is a method of inhibiting thrombosis in a mammal comprising administering to said mammal a composition of comprising a peptide derived from GP1bα that binds 14-3-3, and treating bleeding disorders associated with consumption of platelets and VWF caused by VWF binding to platelets and microthrombus formation. In certain such embodiments, it is contemplated that the mammal is undergoing a procedure during which the mammal's blood is subject to extracorporeal circulation and said administering comprises admixing said composition with the extracorporeal circulating blood in an amount effective to inhibit platelet aggregation in said circulating blood. More particularly, the mammal is subjected to extracorporeal circulation during transplant surgery, abdominal surgery, vascular surgery, or cardiopulmonary bypass surgery. In other embodiments, it is contemplated that the thrombosis is associated with atherosclerosis, myocardial infarction, unstable angina, atrial fibrillation, stroke, renal damage, pulmonary embolism, deep vein thrombosis, percutaneous translumenal coronary angioplasty, disseminated intravascular coagulation, sepsis, artificial organs, shunts or prostheses. In the exemplary methods of the invention, the VWF binding or/and thrombosis are associated with thrombotic thrombocytopenia, other types of microangiopathy, and VWD (type II and platelet type).

The present invention further contemplates kits comprising compositions of the present invention and a delivery device for the administration of the novel compositions described herein. In preferred embodiments, the kits comprise a delivery device that is a preloaded catheter comprising a composition of the claimed invention. The kits may further comprise a second anticoagulant agent in a suitable delivery device.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 1. Effects of a myristoylated phospho-peptide derived from the GPIbα C-terminal 14-3-3 binding site on 14-3-3 binding to GPIb-IX and ristocetin-induced platelet aggregation. (FIG. 1A) A schematic showing the platelet receptor, GPIb-IX and 14-3-3 binding sites. (FIG. 1B) Platelet lysates were incubated with recombinant 14-3-3-conjugated beads or control MBP-conjugated beads in the presence of myristoylated peptides, MPαC, and control peptides, MαC or MαCsc, or DMSO. Bead-bound GPIb-IX was immunoblotted with an anti-GPIbα monoclonal antibody. (FIG. 1C) Platelet-rich plasma (PRP) from healthy donors was preincubated with increasing concentrations of MPαC, and then stimulated with ristocetin to induce platelet aggregation. (FIG. 1D, FIG. 1E)

Ristocetin-induced platelet aggregation in the presence of 100 μM MPαC, myristoylated control peptides, MαC or MαCsc, or vehicle (DMSO) (FIG. 1D) or in the presence of non-myristoylated phospho-peptide (PαC), non-phosphorylated peptide (αC) with identical sequence to MPαC, or myristic anhydride (MA) (FIG. 1E).

Figures 2A, 2B, 2C, 2D, 2E:
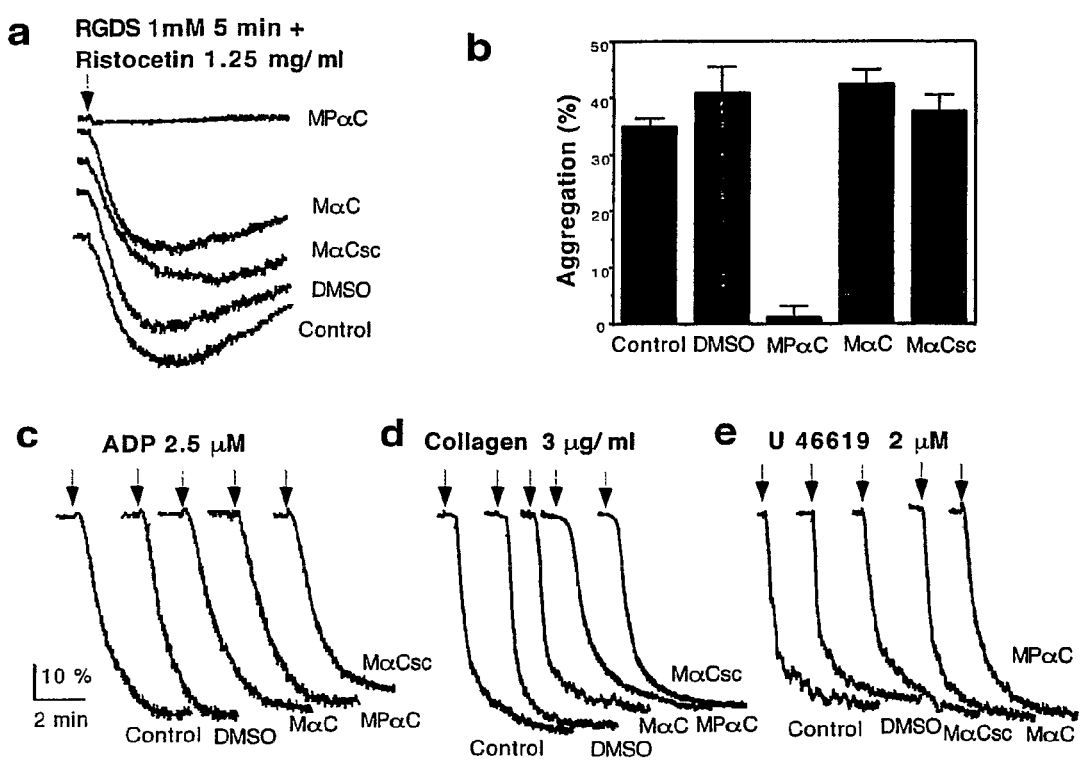

FIG. 2. The 14-3-3 binding peptide, MPαC, specifically inhibits GPIb-IX-dependent platelet agglutination. (FIG. 2A and FIG. 2B) PRP was preincubated with myristoylated peptides, MPαC, MαC or MαCsc, or vehicle (DMSO) together with 1 mM integrin inhibitor, RGDS. Ristocetin (1.25 mg/ml) was added to induce GPIb-IX-specific platelet agglutination. Quantitative data from 4 experiments are shown in FIG. 2B. (FIG. 2C, FIG. 2D and FIG. 2E) PRP was preincubated with MPαC, MαC or MαCsc, or DMSO, then stimulated with collagen (FIG. 2C), ADP (FIG. 2D) or thromboxane A2 analog, U46619 (FIG. 2E), to induce platelet aggregation.

Figures 3A, 3B:
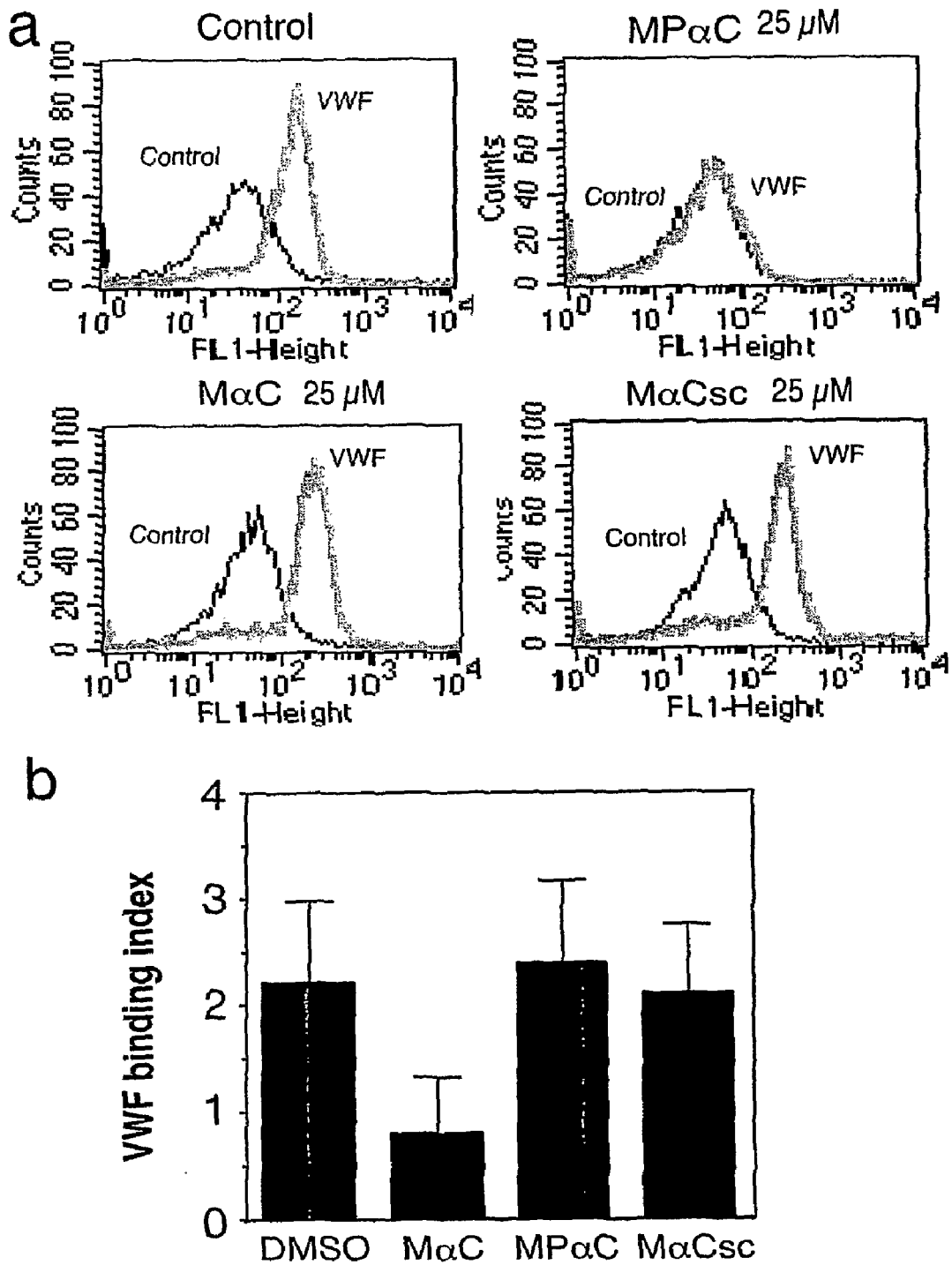

FIG. 3. MPαC inhibits vWF binding to platelets. (FIG. 3A) Washed human platelets were preincubated with MPαC or control peptides MαC or MαCsc and then incubated with 1 mg/ml ristocetin in the presence (vWF) or absence (Control) of 30 μg/ml vWF. vWF binding was detected using FITC-labeled anti-vWF antibody and flow cytometry. (FIG. 3B) Quantitative data from 3 experiments. vWF binding index=Total fluorescence(geomean)/background fluorescence-1.

FIG. 4. Effects of MPαC on vWF-dependent platelet adhesion under flow and bleeding time. (FIG. 4A) Platelets were preincubated with MPαC or control peptides MαC or MαCsc. and then perfused through vWF-coated capillary tubes. Numbers of adherent platelets were counted at 10 randomly selected time frames and locations (mean±SD). (FIG. 4B) Peptides were infused into C57B mice in a double-blinded fashion. After 5 min, tail bleeding times were determined. X, Bleeding time of individual mice. The bars represent median bleeding time of each group. Median bleeding time of MPαC-treated mice was significantly prolonged compared to control peptide-treated mice ($P<0.0001$). (FIG. 4C) A novel 14-3-3-dependent mechanism for regulating receptor function of GPIb-IX.

Figure 5:
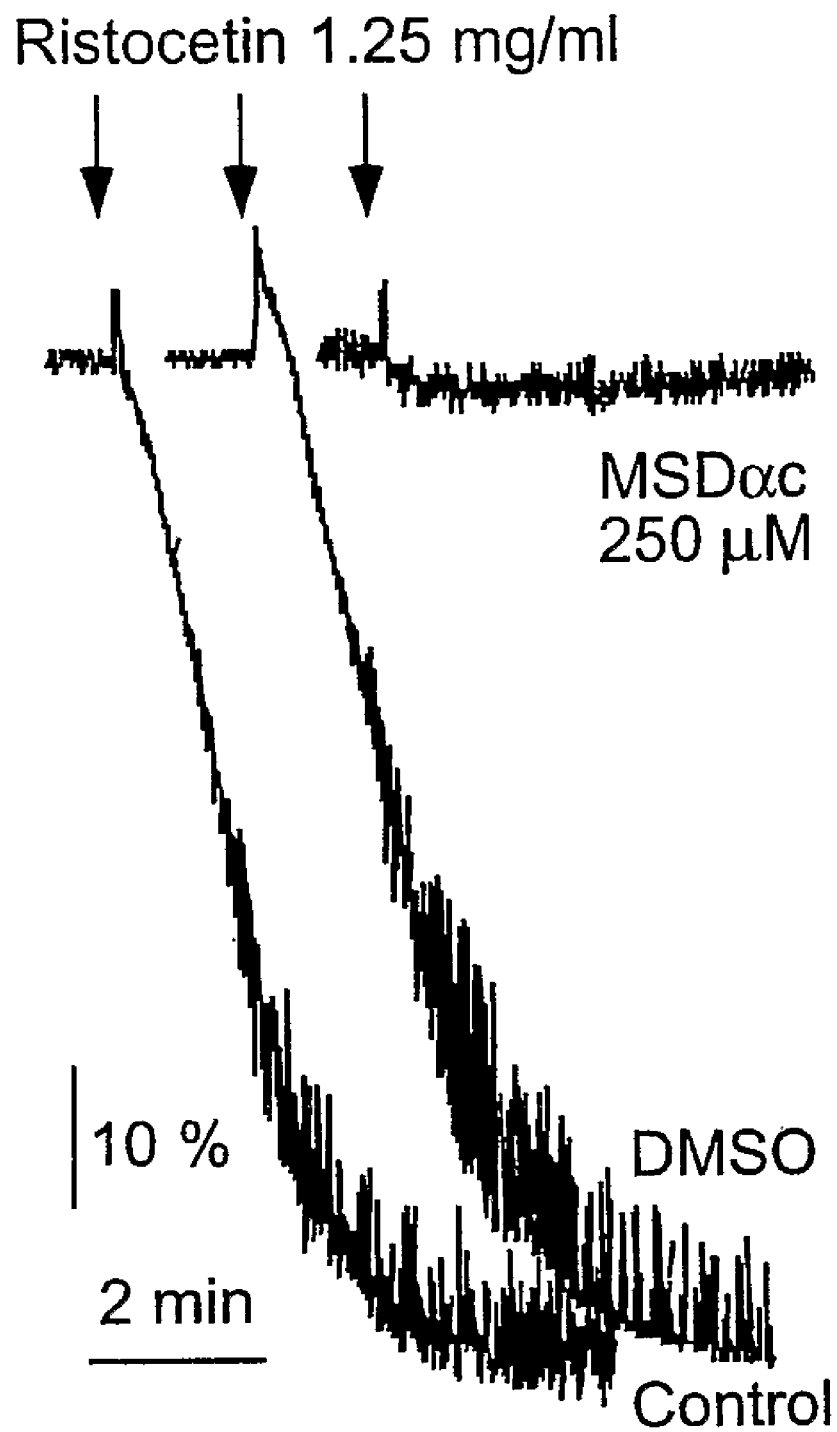

FIG. 5. Inhibition of ristocetin-induced platelet aggregation by MSDαC. Platelet-rich plasma (PRP) was preincubated with or without MSDαC peptide or with DMSO at room temperature for 5 min, and then exposed to ristocetin to induced VWF-dependent platelet aggregation. MSDαC completely inhibited ristocetin-induced platelet aggregation, indicating that this peptide has similar effects as MPαC peptide in inhibiting VWF-induced platelet aggregation.

DESCRIPTION OF THE PREFERRED EMBODIMENTS

Platelet adhesion is essential for thrombosis and hemostasis. While there are a number of anti-thrombotic therapies presently being used, there remains a need for other anti-thrombotic agents.

Platelet adhesion is dependent on the binding of von Willebrand factor (vWF) to its platelet receptor, the glycoprotein (GP) Ib-IX-V complex (GPIb-IX). In the present invention it has been discovered that cell-permeable peptides, and more particularly, phospho-peptides, corresponding to the 14-3-3 binding site of GPIbα inhibit vWF binding to platelets and vWF-mediated platelet adhesion. In addition, the data described herein demonstrate that such peptides also inhibit vWF-dependent platelet agglutination induced by ristocetin. Furthermore, intravenous injection of the peptide compositions causes markedly prolonged bleeding time in mice, indicating a inhibition of hemostatic thrombus formation. Thus, 14-3-3 interaction with GPIbα plays critical roles in vWF binding function of GPIb-IX and hemostatic function of platelets. These results also suggest a new type of anti-platelet drugs that may potentially be useful in treating thrombotic disorders. Methods and compositions for exploiting these findings are described in further detail herein below.

GPIbα-Derived Peptides

As discussed herein throughout and exemplified in the Examples of the present application, peptides derived from the C-terminal domain of GPIbα that retain the ability to bind the intracellular signaling molecule, 14-3-3, inhibit the interaction between 14-3-3 and GPIb-IX, and inhibit the vWF binding to platelets. Moreover, these peptides have a substantial inhibitory effect on GPIb-IX-dependent platelet aggregation. As such, these peptides will be useful in various anti-thrombotic applications including therapies designed for the treatment of pathologies or treatments such as myocardial infarction, unstable angina, atrial fibrillation, stroke, renal damage, percutaneous translumenal coronary angioplasty, disseminated intravascular coagulation, sepsis, pulmonary embolism, deep vein thrombosis, artificial organs implants, shunts implants and prostheses such as artificial heart valves and the like. Indeed, it is contemplated that the compositions of the present invention will be useful as therapeutic agents in a like manner to the present uses of heparin and low molecular weight heparin moieties and/or presently available anti-platelet agents. Furthermore, the compositions of the present invention will be useful in treating thrombotic thrombocytopenic prupura and other types of microangiopathy caused by spontanenous interaction between circulating VWF and platelets. In addition, it is contemplated that the peptides of the invention also will be useful in a variety of combination therapies. Such applications are discussed in further detail elsewhere in the specification.

The sequence of GPIbα is well known to those of skill in the art. (Lopez et al, PNAS 84, 5615-5619, 1987; Du et al., J Biol Chem 271, 7362-7367, 1996; Bodnar et al, J. Biol Chem, 274, 33474-33479, 1999). An exemplary sequence human GPIbα protein sequence is provided at GenBank Acc. No. J02940 (reproduced herein as SEQ ID NO:3, and encoded by a polynucleotide having a nucleic acid sequence of SEQ ID NO:2). The sequence of mature Sequence of mature GPIbα protein is given in SEQ ID NO:4.

While in preferred embodiments, the sequence used herein is derived from human GPIbα, it is contemplated that the sequence also may be derived from another mammalian source such as e.g., mouse (see e.g., mouse GPIbα protein sequence at GenBank Acc. No. NM_010326 for murine protein and nucleic acid sequences). Other sequences for GPIbα proteins are known to those of skill in the art. For example, additional compositions that contain GPIbα those of skill in the art are referred to e.g., U.S. Pat. No. 6,177,059 (incorporated herein by reference in its entirety), which teaches compositions of GPIb as lipid conjugates).

In the present application, a peptide derived from the C-terminal residues 602-610 of GPIbα was prepared and shown to inhibit 14-3-3 interaction with GPIb-IX and to have beneficial inhibitory properties on VWF binding, platelet aggregation and prolonging bleeding times in an in vivo model. This peptide comprises residues SIRYSGHSL (SEQ ID NO: 28). In specific embodiments, it is contemplated that the serine residue derived from $S^{609}$ in the fragment is phosphorylated. Thus, the sequence of the peptide is SIRYSGHpS$^{609}$L (SEQ ID NO: 29) (low case p indicate phosphorylation).

In particularly preferred embodiments, the peptide is derivatized at the C- or N-terminus with a fatty acyl group. In preferred embodiments, the fatty acyl moiety is a myristoyl moiety, however, it is contemplated that other saturated or unsaturated fatty acyl moieties from C2 to C24 may be used as the fatty acyl moieties.

Other preferred peptides produced in the present invention include, but are not limited to myristoylated SIRYSGHDL (SEQ ID NO:8), SIRYSGHEL (SEQ ID NO:9), RYSGHpSL (SEQ ID NO:10), or longer GPIbα cytoplasmic domain sequence containing the 14-3-3 binding site. The cytoplasmic domain of GPIbα has the following sequence:

(SEQ ID NO: 11)
SWVGHVKPQALDSGQGAALTTATQTTHLELQRGRQVTVPRA

WLLFLRGSLPTFRSSLFLWVRPNGRVGPLVAGRRPSALSQGRGQDLLSTV

SIRYSGHSL.

The peptides used in the present invention may be peptides of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acid residues in length derived from the C-terminal portion of the GPIbα as long as the peptide retain the ability to bind 14-3-3. Therefore, other exemplary peptides may include, e.g., VSIRYSGHSL (SEQ ID NO:12); TVSIRYSGHSL (SEQ ID NO:13); STVSIRYSGHSL (SEQ ID NO:14); LSTVSIRYSGHSL (SEQ ID NO:15); LLSTVSIRYSGHSL (SEQ ID NO:16); DLLSTVSIRYSGHSL (SEQ ID NO:17); QDLLSTVSIRYSGHSL (SEQ ID NO:18); GQDLLSTVSIRYSGHSL (SEQ ID NO:19); RGQDLLSTVSIRYSGHSL (SEQ ID NO:20); GRGQDLLSTVSIRYSGHSL (SEQ ID NO:21); QGRGQDLLSTVSIRYSGHSL (SEQ ID NO:22); SQGRGQDLLSTVSIRYSGHSL (SEQ ID NO:23); LSQGRGQDLLSTVSIRYSGHSL (SEQ ID NO:24); ALSQGRGQDLLSTVSIRYSGHSL (SEQ ID NO:25); SALSQGRGQDLLSTVSIRYSGHSL (SEQ ID NO:26); PSALSQGRGQDLLSTVSIRYSGHSL (SEQ ID NO:27). As one skilled in the art will readily recognize these peptides are derived from the C-terminus of the sequence of SEQ ID NO:4. In particularly preferred embodiments, one or more of the serine residues is substituted with an aspartic acid or glutamic acid residue in order to simulate the effect of phosphorylation of those residues. Thus, other exemplary peptides of the invention include e.g., any of sequences VSIRYSGHSL (SEQ ID NO:12); TVSIRYSGHSL (SEQ ID NO:13); STVSIRYSGHSL (SEQ ID NO:14); LSTVSIRYSGHSL (SEQ ID NO:15); LLSTVSIRYSGHSL (SEQ ID NO:16); DLLSTVSIRYSGHSL (SEQ ID NO:17); QDLLSTVSIRYSGHSL (SEQ ID NO:18); GQDLLSTVSIRYSGHSL (SEQ ID NO:19); RGQDLLSTVSIRYSGHSL (SEQ ID NO:20); GRGQDLLSTVSIRYSGHSL (SEQ ID NO:21); QGRGQDLLSTVSIRYSGHSL (SEQ ID NO:22); SQGRGQDLLSTVSIRYSGHSL (SEQ ID NO:23); LSQGRGQDLLSTVSIRYSGHSL (SEQ ID NO:24); ALSQGRGQDLLSTVSIRYSGHSL (SEQ ID NO:25); SALSQGRGQDLLSTVSIRYSGHSL (SEQ ID NO:26); PSALSQGRGQDLLSTVSIRYSGHSL (SEQ ID NO:27) or other C-terminal fragments of a sequence of SEQ ID NO:4 in which one or more of the serine or threonine residues has been substituted with an aspartic acid or a glutamic acid residue. Such peptides are preferably myristoylated. In an exemplary embodiment, a myristoylated peptide with the sequence of C13H27CONH-SIRYSGHDL was synthesized and named "MSDαC". The amino acid sequence of this peptide is derived from the GPIbα C-terminal SIRYSGHpSL sequence with a mutation that replaces phosphorylated serine 609 residue with an aspartic acid to simulate phosphoserine. Platelet-rich plasma (PRP) were preincubated with or without MSDαC peptide or with DMSO at room temperature for 5 min, and then exposed to ristocetin to induced VWF-dependent platelet aggregation. MSDαC completely inhibited ristocetin-induced platelet aggregation, indicating that this peptide has similar effects as MPαC peptide in inhibiting VWF-induced platelet aggregation (see FIG. 5). Similar such studies may be performed with any other C-terminal residue of the sequence of SEQ ID NO:4 as described herein.

In those embodiments in which the GPIbα-derived phospho-peptide will be delivered as a therapeutic agent, it is contemplated that the GPIbα derived, myristoylated phospho-peptides may be modified to enhance their uptake, circulation, and/or other modifications to render the peptides more therapeutically effective. Thus, it may be desirable to prevent the degradation of the peptides in order to prolong the effects thereof, and as, such prolong the effects of the GPIbα-derived peptide as an inhibitor of platelet aggregation and the like in the circulation of an individual suffering from or at risk of developing e.g., thrombosis. This may be achieved through the use of non-hydrolyzable peptide bonds, which are known in the art, along with procedures for synthesis of peptides containing such bonds. Non-hydrolyzable bonds include —[CH$_2$NH]— reduced amide peptide bonds, —[COCH$_2$]— ketomethylene peptide bonds, —[CH(CN)NH]— (cyanomethylene)amino peptide bonds, —[CH$_2$CH(OH)]— hydroxyethylene peptide bonds, —[CH$_2$O]— peptide bonds, and —[CH$_2$S]— thiomethylene peptide bonds (see e.g., U.S. Pat. No. 6,172,043).

It is also contemplated that myristoylation of the peptide confers membrane interaction and/or membrane permeability to this peptide. Thus, other moiety or method that renders this peptide membrane-permeable or membrane attachable may also be used for the effectiveness of this peptide in inhibiting 14-3-3 function and the function of GPIb-IX to mediate VWF binding, platelet adhesion and activation, and thrombus formation. Example of the method that renders peptide membrane permeable include the signal peptides, carrier peptides and other lipophilic moieties.

GPIbα-derived proteins useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (Int. J Pep. Protein Res. 36:392-399, 1990) and Rivera-Baeza et al. (Neuropeptides 30:327-333, 1996) are also known in the art.

Furthermore, nonpeptide analogs of the GPIbα-derived peptides of the invention that provide a stabilized structure or lessened biodegradation, are also contemplated. Peptide mimetic analogs can be prepared based on a GPIbα peptide by replacing one or more amino acid residues of the protein of interest by nonpeptide moieties. Preferably, the nonpeptide moieties permit the peptide to retain its natural confirmation, or stabilize a preferred, e.g., bioactive confirmation and an overall positive charge. One example of methods for preparation of nonpeptide mimetic analogs from peptides is described in Nachman et al., Regul. Pept. 57:359-370 (1995). The term "peptide" as used herein embraces nonpeptide analogs, mimetics and modified peptides.

The GPIbα derived peptides used in the therapeutic methods of the present invention may be modified in order to improve their therapeutic efficacy. Such modification of therapeutic compounds may be used to decrease toxicity, increase circulatory time, or modify biodistribution. A strategy for improving drug viability is the utilization of water-soluble polymers. Various water-soluble polymers have been shown to modify biodistribution, improve the mode of cellular uptake, change the permeability through physiological barriers, and modify the rate of clearance from the body. (Greenwald et al., Crit Rev Therap Drug Carrier Syst. 2000; 17:101-161; Kopecek et al., J Controlled Release, 74:147-158, 2001). To achieve either a targeting or sustained-release effect, water-soluble polymers have been synthesized that contain drug moieties as terminal groups, as part of the backbone, or as pendent groups on the polymer chain.

Polyethylene glycol (PEG), has been widely used as a drug carrier, given its high degree of biocompatibility and ease of modification. Harris et al., Clin Pharmacokinet. 2001; 40(7): 539-51 Attachment to various drugs, proteins, and liposomes has been shown to improve residence time and decrease toxicity. (Greenwald et al., Crit Rev Therap Drug Carrier Syst. 2000; 17:101-161; Zalipsky et al., Bioconjug Chem. 1997; 8:111-118). PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications (Nathan et al., Macromolecules. 1992; 25:4476-4484; Nathan et al., Bioconj Chem. 1993; 4:54-62).

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate.

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the GPIbα derived proteins described herein for therapeutic delivery. Methods of Making and Isolating GPIbα Derived Peptides The present invention provides GPIbα-based proteins and peptides either as medicaments themselves, or for use in combinations with other hemostatic agents. Such GPIbα peptides may be produced by conventional automated peptide synthesis methods or by recombinant expression. General principles for designing and making proteins are well known to those of skill in the art.

A. Peptide Synthesis

The preferred method for making the peptides used in the present invention is in solution or on a solid support in accordance with conventional fmoc-based techniques. The peptides can be prepared from a variety of synthetic or enzymatic schemes, which are well known in the art. Where short peptides are desired, such peptides are prepared using automated peptide synthesis in solution or on a solid support in accordance with conventional techniques. Various automatic synthesizers are commercially available and are used in accordance with known protocols. See, for example, Stewart and Young, Solid Phase Peptide Synthesis, 2d. ed., Pierce Chemical Co., (1984); Tam et al., J. Am. Chem. Soc., 105:6442, (1983); Merrifield, Science, 232: 341-347, (1986); and Barany and Merrifield, The Peptides, Gross and Meienhofer, eds, Academic Press, New York, 1-284, (1979); Fields, (1997) Solid-Phase Peptide Synthesis. Academic Press, San Diego); Andersson et al., Large-scale synthesis of peptides. Biopolymers (Pept. Sci.), 55, 227-250 (2000); Burgess et al., DiS-SiMiL: Diverse Small Size Mini-Libraries applied to simple and rapid epitope mapping of a monoclonal antibody. J. Pept. Res., 57, 68-76, (2001); Peptides for the New Millennium, Fields, J. P. Tam & G. Barany (Eds.), Kluwer Academic Publisher, Dordrecht. Numerous other documents teaching solid phase synthesis of peptides are known to those of skill in the art and may be used to synthesis epitope arrays from any allergen.

For example, the peptides are synthesized by solid-phase technology employing an exemplary peptide synthesizer such as a Model 433A from Applied Biosystems Inc. This instrument combines the FMOC chemistry with the HBTU activation to perform solid-phase peptide synthesis. Synthesis starts with the C-terminal amino acid. Amino acids are then added one at a time till the N-terminus is reached. Three steps are repeated each time an amino acid is added. Initially, there is deprotection of the N-terminal amino acid of the peptide bound to the resin. The second step involves activation and addition of the next amino acid and the third step involves deprotection of the new N-terminal amino acid. In between each step there are washing steps. This type of synthesizer is capable of monitoring the deprotection and coupling steps.

At the end of the synthesis the protected peptide and the resin are collected, the peptide is then cleaved from the resin and the side-chain protection groups are removed from the peptide. Both the cleavage and deprotection reactions are typically carried out in the presence of 90% TFA, 5% thioanisole and 2.5% ethanedithiol. After the peptide is separated from the resin, e.g., by filtration through glass wool, the peptide is precipitated in the presence of MTBE (methyl t-butyl ether). Diethyl ether is used in the case of very hydrophobic peptides. The peptide is then washed a plurality of times with MTBE in order to remove the protection groups and to neutralize any leftover acidity. The purity of the peptide is further monitored by mass spectrometry and in some case by amino acid analysis and sequencing.

The peptides also may be modified, and such modifications may be carried out on the synthesizer with very minor interventions. An amide could be added at the C-terminus of the peptide. An acetyl group could be added to the N-terminus. Biotin, stearate and other modifications could also be added to the N-terminus.

The purity of any given peptide, generated through automated peptide synthesis or through recombinant methods, is typically determined using reverse phase HPLC analysis. Chemical authenticity of each peptide is established by any method well known to those of skill in the art. In certain embodiments, the authenticity is established by mass spectrometry. Additionally, the peptides also are quantified using amino acid analysis in which microwave hydrolyses are conducted. In one aspect, such analyses use a microwave oven such as the CEM Corporation's MDS 2000 microwave oven. The peptide (approximately 2 μg protein) is contacted with e.g., 6 N HCl (Pierce Constant Boiling e.g., about 4 ml) with approximately 0.5% (volume to volume) phenol (Mallinckrodt). Prior to the hydrolysis, the samples are alternately evacuated and flushed with $N_2$. The protein hydrolysis is conducted using a two-stage process. During the first stage, the peptides are subjected to a reaction temperature of about 100° C. and held that temperature for 1 minute. Immediately after this step, the temperature is increased to 150° C. and held at that temperature for about 25 minutes. After cooling, the samples are dried and amino acid from the hydrolysed peptides samples are derivatized using 6-aminoquinolyl-N-hydroxysuccinimidyl carbamate to yield stable ureas that fluoresce at 395 nm (Waters AccQ Tag Chemistry Package). In certain aspects, the samples are analyzed by reverse phase HPLC and quantification is achieved using an enhanced integrator.

In preferred embodiments, the peptides of the present invention are made using FMOC solid-phase synthetic methods such as those described above. However, in certain embodiments, it is contemplated that those skilled in the art also may employ recombinant techniques for the expression of the proteins wherein a nucleotide sequence which encodes a peptide of the invention is inserted into an expression vector, transformed or transfected into an appropriate host cell and cultivated under conditions suitable for expression as described herein below. Recombinant methods are especially preferred for producing longer polypeptides that comprise peptide sequences of the invention. For example, see U.S. Pat. No. 5,298,293 for general methods of producing GPIbα proteins via recombinant methods, e.g., by culturing prokaryotic and eukaryotic cells transformed by a vector for the expression of human GPIbα. Those of skill in the art are particularly referred to U.S. Pat. No. 5,340,727, which describes DNA expression vectors encoding a peptide which encodes the amino acid sequence of the amino terminal region of platelet membrane glycoprotein Ibα; as well as mammalian host cells transformed by said vectors; and a process for producing a peptides from the same. The methods disclosed therein will be useful in the recombinant production of C-terminal peptides that comprise a sequence of SEQ ID NO:1 as part or all of the peptides for the purposes of the present invention.

B. Protein Purification

It will be desirable to purify the peptides of the present invention. Protein purification techniques are well known to those of skill in the art. These techniques involve, at one level, the crude fractionation of the cellular milieu to polypeptide and non-polypeptide fractions. Having separated the peptides or polypeptides of the invention from other proteins, the polypeptides or peptides of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Particularly efficient methods of purifying peptides include fast protein liquid chromatography (FPLC) and high performance liquid chromatography (HPLC).

Certain aspects of the present invention concern the purification, and in particular embodiments, the substantial purification, of an encoded polypeptide, protein or peptide. The term "purified polypeptide, protein or peptide" as used herein, is intended to refer to a composition, isolated from other components, wherein the polypeptide, protein or peptide is purified to any degree relative to its naturally-obtainable state. A purified polypeptide, protein or peptide therefore also refers to a polypeptide, protein or peptide, free from the environment in which it may naturally occur.

Generally, "purified" will refer to a polypeptide, protein or peptide composition that has been subjected to fractionation to remove various other components, and which composition substantially retains its expressed biological activity. Where the term "substantially purified" is used, this designation will refer to a composition in which the polypeptide, protein or peptide forms the major component of the composition, such as constituting about 50%, about 60%, about 70%, about 80%, about 90%, about 95% or more of the proteins in the composition.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified polypeptide, protein or peptide.

Disorders to be Treated

It is contemplated that the compositions of the present invention will be used in the treatment of a variety of disorders in which there is a need to prevent or treat thrombosis and subsequent decrease or loss of blood flow. The examples of thrombotic disorders include but not limited to atherosclerosis, myocardial infarction, stroke, and kidney ischemia, and thrombosis in any part of the mammalian body. The composition of the present invention will also be used in the prevention and treatment of microangiopathy in which formation of microthrombi or VWF binding to platelets causes excessive consumption of platelets and/or VWF leading to subsequent bleeding diathesis. Examples of latter disorders include but not limited to thrombotic thrombocytopenic purpura, type II and platelet type von Willebrand disease (VWD). The peptides of the present invention, e.g., peptides comprising SEQ ID NO:1 or conservative variants thereof, inhibit VWF-dependent platelet adhesion and aggregation. The peptides have been shown to be useful in prolonging bleed time in a mammal and as such, will be useful as anti-thrombotic agents both in therapeutic and prophylactic methods. As such, these peptides will be useful as anticoagulant agents and/or anti-platelet agents. As explained herein throughout there are at least two types of medicaments that may arise from the present invention. Firstly, the present invention provides compositions that comprise GPIbα fragments described herein above as anti-thrombotic agents alone. Alternatively, the peptides may be combined with other therapeutic agents for the treatment of thrombosis and other disorders of the cardiovascular circulatory system that require and increase in the flow or reducing blockage of the vessels.

The peptide in this invention may also be used to block 14-3-3 interaction with other ligands of 14-3-3 that are present in all eukaryotic cells and are potentially important in other cellular functions including but not limiting to cell protection against apoptosis, cell proliferation, cell cycle and intracellular signal transduction as described in the literature (Fu et al., Annu Rev Pharmacol Toxicol 40, 617-647, 2000).

A. Treatment Using GPIbα Fragments

GPIbα fragments described herein have an anti-platelet activity. Therefore, the fragments or combinations will be useful for the treatment of any disorder that is presently treated using anticoagulant therapy, such as by the use of heparin-based medicaments or other antiplatelet agents such as e.g., Aggrastat™, Aggrenox™, Agrylin™, Flolan™, Integrilin™, Presantine™, Plavix™, Pletal™, REoPro™, Coumdin, Fragmin™, Hep-Lock™, Lovenox™, Miradon™ and the like. Such disorders include pulmonary embolism, unstable angina, myocardial infarction, deep vein thrombosis, atrial fibrillation with embolization, acute and chronic coagulopathies (disseminated intravascular coagulation), for prevention of clotting in arterial and cardiac surgery, for prophylaxis and treatment of peripheral arterial embolism, The GPIba-derived peptide described in the present invention will be also be used to treat thrombotic thrombocytopic purpura, other types of microangiopathy that are mediated by spontaneous interaction between VWF and platelets, platelet type or type IIb von Willebrand diseases in which there is an increased binding of VWF to platelets (either caused by a defect in GPIb or in VWF). The compositions described herein may be useful as anti-platelet agents in blood transfusions, extracorporeal circulation, dialysis procedures as well as blood sampling for laboratory procedures. The compositions also may be used to maintain the patency of an indwelling venipucture device that is being used for intermittent injection or infusion therapy or blood sampling. The compositions may be particularly useful in surgical procedures to prevent the formation of blood clots. Such indications are particularly desirable for patients undergoing abdominal surgery to reduce the risk of thromboemolic complications, patients undergoing knee or hip replacement therapy during and following the replacement procedure, as well as a general prophylactic to prevent clot formation at a later stage. The compositions also may be useful in the treatment of subjects that are under risk of thromboembolic complications due to severely restricted mobility e.g., during acute illness. Any such disorders may be readily treated by the compositions described herein. The therapeutic methods include both medical therapeutic and/or prophylactic administration, as appropriate.

As used herein, the term "inhibits platelet aggregation" includes its generally accepted meaning which includes prohibiting, slowing, or reducing the severity or degree of platelet aggregation. Such an inhibition may be measured as a function of time taken for a given sample to coagulate. In other embodiments, animal models of thrombosis. Methods of determining the efficacy of the agents include coagulation testing, monitoring the time of bleeding, determining hemoglobin levels of an animal and the like.

For example, clots may be analyzed in vitro in an assay in which citrated plasma (e.g., 1100 µl) is mixed with 15 µl of radiolabelled human fibrinogen (e.g., about 40,000 cpm/clot). plasma (35 µl) is mixed with 35 µl of Tris-buffered saline (TBS) containing 10 mM CaCl2 and thrombin (1 U/ml) in twelve 65-mm plastic tubes and clotted for 1 hour at 37° C. The clots are washed in TBS, the supernatant is removed, and then 100 µl of TBS or 25 µg of purified plasminogen activator fragment is added to tubes in duplicate. Clot lysis is initiated by adding 0.1 U of plasminogen activator per tube. The clots are incubated at 37° C. for 5 hours and the amount of lysis was determined by sampling for the release of radiolabeled fibrin degradation products into the supernatant, as described (Reed, G. L. III et al., Proc. Natl. Acad. Sci. USA 87:1114-1118 (1990)).

Experimental models of pulmonary embolism are known to those of skill in the art. In such a model a small mammal, e.g., a rat is an anesthetized by intramuscular injection (0.4 ml) of a mixture of ketamine and acepromazine (two parts acepromazine [10 mg/ml] to one part ketamine [100 mg/ml]). Intraperitoneal injections are repeated as necessary to keep the animals anesthetized. After an anterior midline incision is made in the neck, the jugular vein and the carotid artery are exposed by blunt dissection and cannulated with 20 G catheters that are secured at the proximal and distal ends with 4-0 silk sutures. The catheters are capped with three-way stopcocks.

Citrated human plasma is mixed with 125I-fibrinogen to achieve about 1,000,000 cpm/ml. Individual clots are formed by mixing 125I-fibrinogen-labeled plasma (45 µl) with 2.5 µl of bovine thrombin (100 U/ml) and 2.5 µl of calcium chloride (0.4 M). These clots are incubated at 37° C. for 90 minutes, compressed, and washed thoroughly with saline three times to remove unbound proteins. The radioactive content of the clots is measured in a gamma counter immediately before clot injection. Blood samples are drawn at base line and at the end of the experiment. Sodium iodide (10 mg) is injected to block thyroid uptake. Clots are embolized into the lungs by injection through the internal jugular vein. Animals weighing less than 1 kg received three clots; those weighing 1 kg or more received four clots. Successful embolization is evidenced by the accumulation of radioactivity in the thorax. After the clots are injected, the animals are turned on their sides to ease breathing.

All animals receive weight-adjusted heparin at 100 U/kg (bolus), a dose sufficient to keep the activated partial thromboplastin time (aPTT) above 150 seconds throughout the procedure. The anti-platelet agent being tested is administered intravenously as a single dose (e.g., 20 mg/kg). The plasminogen activator is given as a continuous infusion over 2 hours (1 or 2 mg/kg in 5 ml normal saline). Animals are observed for a total of four hours after pulmonary embolization and then killed by lethal injection of anesthesia or by $CO_2$ inhalation. The thorax is dissected and all intrathoracic structures are removed for gamma counting to detect residual thrombi. The percentage of clot lysis was determined for each animal by dividing the total residual radioactivity in the thorax (cpm) by that in the initial thrombi. In addition to the above methods, specific examples of assays for determining platelet adhesion, animal bleeding times and platelet aggregation are provided in Example 1.

Of course, it should be understood that the GPIbα fragments may form part of a therapeutic regimen in which the GPIbα-based peptide treatment is used in combination with a plurality of other therapies for the given disorder. As such, combination therapy is specifically contemplated. In combination therapy, the GPIbα-based peptide composition is administered with another anticoagulant or anti-platelet agent. Such agents are well known to those of skill in the art and include, but are not limited to Aggrastat™, Aggrenox™, Agrylin™, Flolan™, Integrilin™, Presantine™, Plavix™, Pletal™, REoPro™, Coumdin, Fragmin™, Hep-Lock™, Lovenox™, Miradon™, tinzaparin, certoparin, parnaparin, nadroparin, ardeparin, enoxaparin, reviparin, reviparin, dalteparin, and fraxiparin. In specific embodiments, the one or more of the compositions may be provided in a catheter.

From the above discussion, it should be understood that the disorder that may be treated by the compositions of the present invention are limited only by the fact that the disorder needs a therapeutic intervention which inhibits platelet aggregation. The doses of the agent may be modified for each individual subject. For particular guidance on the routes of administration, and uses those of skill in the art are referred to the Physician's Desk Reference for generalized descriptions of formulations, routes of administration and patient monitoring used for agents such as Aggrastat™ (see e.g., entry at pages 1933-1937, PDR, $57^{th}$ Edn., 2003), Aggrenox™ (see e.g., entry at pages 1023-1026, PDR, $57^{th}$ Edn., 2003), Agrylin™ (see e.g., entry at pages 3142-3143, PDR, $57^{th}$ Edn., 2003), Flolan™ (see e.g., entry at pages 1516-1521, PDR, $57^{th}$ Edn., 2003), Integrilin™ (see e.g., entry at pages 2138-2142, PDR, $57^{th}$ Edn., 2003), Presantine™ (see e.g., entry at pages 1052-2053, PDR, $57^{th}$ Edn., 2003), Plavix™ (see e.g., entry at pages 1098-1101, PDR, $57^{th}$ Edn., 2003), Pletal™ (see e.g., entry at pages 2780-2782, PDR, $57^{th}$ Edn., 2003), REoPro™ (see e.g., entry at pages 1866-1870, PDR, $57^{th}$ Edn., 2003), Coumdin™ (see e.g., entry at pages 1074-1079, PDR, $57^{th}$ Edn., 2003), Fragmin™ (see e.g., entry at pages 2750-2754, PDR, $57^{th}$ Edn., 2003), Hep-Lock™ (see e.g., entry at pages 1284-1288, PDR, $57^{th}$ Edn., 2003), Lovenox™ (see e.g., entry at pages 739-744, PDR, $57^{th}$ Edn., 2003), Miradon™ (see e.g., entry at pages 3051-3052, PDR, $57^{th}$ Edn., 2003). These entries in the PDR are provided to show the level of skill in the art relating to formulating and using compositions as anticoagulants and anti-platelet agents.

Specific amounts and route of GPIbα-based anti-platelet agent administered may vary, and will be determined in the clinical trial of these agents. However, it is contemplated that those skilled in the art may administer ~10 nmol/g body weight of the above described agents to mice via intraveneous route to achieve prolonged bleeding time.

Pharmaceutical Compositions

Pharmaceutical compositions for administration according to the present invention can comprise either fragments of GPIbα alone as described above or in combination with other anticoagulants or antiplatelet agents. Regardless of whether the active component of the pharmaceutical composition is a GPIbα fragment alone, a GPIbα fragment in combination with another active agent of interest, each of these preparations is in some aspects provided in a pharmaceutically acceptable form optionally combined with a pharmaceutically acceptable carrier. These compositions are administered by any methods that achieve their intended purposes. Individualized amounts and regimens for the administration of the compositions for the treatment of the given disorder are determined readily by those with ordinary skill in the art using assays that are used for the diagnosis of the disorder and determining the level of effect a given therapeutic intervention produces.

It is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is understood and determinable by one of skill in the art, without undue experimentation. This typically involves adjustment of a standard dose, e.g., reduction of the dose if the patient has a low body weight.

The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

In some aspects, the compositions of the invention are formulated into suitable pharmaceutical compositions, i.e., in a form appropriate for in vivo applications in the therapeutic intervention of a given disease. Generally, this will entail preparing compositions that are essentially free of pyrogens, as well as other impurities that could be harmful to humans or animals. In some aspects, the compositions are prepared for administration directly to the lung. These formulations are for oral administration via an inhalant, however, other routes of administration are contemplated (e.g. injection and the like). An inhaler device is any device useful in the administration of the inhalable medicament. Examples of inhaler devices include nebulizers, metered dose inhalers, dry powder inhalers, intermittent positive pressure breathing apparatuses, humidifiers, bubble environments, oxygen chambers, oxygen masks and artificial respirators. As the GPIbα fragments are relatively short peptides, such fragments may be well suited to formulation as an inhalable medicament. Therefore, it is particularly contemplated that the GPIbα fragments or the GPIbα fragments conjugated to active agents will be formulated as inhalable compositions. Further, the compositions of the invention include kits in which the inhalable medicament is formulated in a container suitable for administration via inhalation.

One will generally desire to employ appropriate salts and buffers to render the compositions stable and allow for uptake of the compositions at the target site. Generally, the pharmaceutical compositions of the invention are provided in lyophilized form to be reconstituted prior to administration. Alternatively, the pharmaceutical compositions may be formulated into tablet form or solution. Buffers and solutions for the reconstitution of the pharmaceutical compositions may be provided along with the pharmaceutical formulation to produce aqueous compositions of the present invention for administration. Such aqueous compositions will comprise an effective amount of each of the therapeutic agents being used, dissolved or dispersed in a pharmaceutically acceptable carrier or aqueous medium. Such compositions also may be useful in combination with surgical intervention to reduce the risk of blood clot development during surgery.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also are incorporated into the compositions.

Methods of formulating proteins and peptides for therapeutic administration also are known to those of skill in the art. Administration of these compositions according to the present invention will be via any common route so long as the target tissue is available via that route. Most commonly, these compositions are formulated for oral administration, such as by an inhalant. However, other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site also is used particularly when oral administration is problematic. The treatment may consist of a single dose or a plurality of doses over a period of time.

In certain embodiments, the active compounds are prepared for administration as solutions of free base, acid or pharmacologically acceptable salts in water suitably mixed with a surfactant, such as hydroxypropylcellulose. Dispersions also are prepared in glycerol, liquid polyethylene glycols, and mixtures thereof and in oils or other solvents. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. In some aspects, the carrier is a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also are incorporated into the compositions.

In some aspects, the compositions of the present invention are formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also are derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. In certain embodiment, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

The present invention also contemplated kits for use in the treatment of various disorders. Such kits include at least a first composition comprising the GPIbα proteins/peptides described above in a pharmaceutically acceptable carrier. In specific embodiments, the composition is provided in a catheter. Another component is a second therapeutic agent for the treatment of the disorder along with suitable container and vehicles for administrations of the therapeutic compositions. The kits may additionally comprise solutions or buffers for effecting the delivery of the first and second compositions. The kits may further comprise catheters, syringes or other delivering devices for the delivery of one or more of the compositions used in the methods of the invention. The kits may further comprise instructions containing administration protocols for the therapeutic regimens.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Synthetic peptides. Myristoylated peptides, MPαC ($C_{13}H_{27}$CONH-SIRYSGHpSL), MαC ($C_{13}H_{27}$CONH-SIRYSGHSL), MαCsc ($C_{13}H_{27}$CONH-LSISYGSHR), and non-myristoylated peptides, PαC (SIRYSGHpSL), and αC (SIRYSGHSL) were synthesized by standard fmoc solid-phase synthetic methods by the Protein Research Laboratory, University of Illinois at Chicago. The peptides were more than 95% in purity. Myristoylated peptides were dissolved in DMSO.

Platelet preparation and aggregation. Blood was drawn from healthy donors, and was anti-coagulated with 1/10 volume of 3.8% trisodium citrate. Platelet-rich plasma (PRP) was obtained by centrifugation at 300×g for 20 min at 22° C. Platelet aggregation was measured using a turbidometric platelet aggregometer at 37° C. with a stirring speed at 1000 rpm. To examine the effects of peptides, various concentrations of each peptide was preincubated with platelets at 22° C. for 5 min. In some experiments, intergrin inhibitor RGDS (1 mM) was also added to exclude the roles of β3 integrins.

14-3-3 binding to GPIb-IX. Binding of GPIb-IX to 14-3-3-conjugated beads were performed as previously described (Du et al., J. Biol. Chem., 271:7362-7367 (1996)). Briefly, 14-3-3-conjugated Sepharose 4B beads and maltose-binding protein (MBP)-conjugated control beads were preincubated with various concentrations of synthetic peptides at 4° C. for 1 h, and then with platelet lysates for an additional 1 h. The beads were washed three times. Bound GPIb-IX was detected by Western blot with a monoclonal antibody against GPIbα, WM23.

Flow cytometry analysis of VWF binding to platelets. Flow cytometry analysis of vWF binding to platelets has been described previously 8,9. Washed platelets ($1.0 \times 10^7$/ml) were prepared as described previously (Englund et al., J. Biol. Chem., 276:16952-16959 (2001); Bodnar et al., J. Biol. Chem. 277:47080-47087 (2002)), and resuspended in phosphate-buffered saline (PBS) solution (0.01 M $NaH_2PO_4$, 0.15 M NaCl, pH 7.4) containing 10 mM EDTA and 1% BSA. Platelets were preincubated with various concentrations of synthetic peptides at 22° C. for 10 min before incubating with purified vWF (35 µg/ml) and ristocetin (1.0 mg/ml) at 22° C. for 30 min. Platelets were washed once, further incubated in the same buffer containing 10 µg/ml FITC-labeled SZ-29 in the dark at 22° C. for 30 min and then analyzed by flow cytometry. As negative controls, platelets were incubated in the presence of ristocetin alone then incubated with FITC-labeled SZ29.

Platelet adhesion under flow. Washed platelets ($3 \times 10^8$/ml) were preincubated with various concentrations of synthetic peptides at 22° C. for 10 min, the platelets were perfused into the vWF-coated glass capillaries using a PhD syringe pump (Harvard Apparatus Inc.) at various shear rates for 8 min. Transient adhesion of platelets on the vWF-coated surface was recorded on video cassette recorder. Adherent platelets were counted in 10 randomly selected fields of 0.25 $mm^2$ within a 10 second time period.

Tail-bleeding time. Bleeding times were performed with 6-8-wk-old adult C57 black mice anesthetized with an intraperitoneal injection of avertin. The internal jugular vein was surgically exposed, and a total volume of 50 µl of a peptide (5 mM) was infused using a 27 G needle. Experiments were performed in a double-blinded fashion. After 5 min, tails were amputated 5 mm from the tail tip, and immersed in a tube containing 0.15M NaCl maintained at 37° C. Bleeding was visually followed and timed. Maximum bleeding time allowed was 10 min after which the tail was cauterized. Statistical differences between the groups were examined using Mann-Whitney test and InStat software.

Example 2

Results and Discussion

Binding of subendothelial-bound von Willebrand factor (vWF) to its platelet receptor, glycoprotein Ib-IX (GPIb-IX), is a critical initiating step in platelet adhesion and activation (Ruggeri, Prog. Hemost. Thromb., 10:35-68 (1991); Ware, Thromb. Haemost., 79:466-478 (1998)). Despite the early belief that GPIb-IX is constitutively active in binding vWF, increasing evidence suggests that ligand binding function of GPIb-IX may be regulated by intracellular signals (Coller, Blood, 57:846-855 (1981); Englund et al., J. Biol. Chem., 276:16952-16959 (2001); Bodnar et al., J. Biol. Chem., 277: 47080-47087 (2002)). It was previously shown that the cytoplasmic domain of GPIbα interacts with an intracellular signaling molecule, 14-3-3, and that a 14-3-3 binding site is located at the C-terminal domain of GPIbα ($S^{602}$IRYSGHpSL$^{610}$ SEQ ID NO:1) (Du et al., J. Biol. Chem., 271:7362-7367 (1996); Bodnar et al., J. Biol. Chem., 274:33474-33479 (1999)) (FIG. 1A). To study the role of 14-3-3 in regulating GPIb-IX function, a cell-permeable myristoylated phospho-peptide named MPαC ($C_{13}H_{27}$CONH-SIRYSGHpSL) was prepared. This peptide was based on the sequence of 14-3-3 binding site in the C-terminal region of GPIbα with phosphorylation at the serine corresponding to $Ser^{609}$. A myristoylated non-phosphorylated peptide with the identical sequence as above (MαC) and a myristoylated scrambled peptide (MαCsc) also were prepared as controls.

To examine if the above peptides interfere with 14-3-3 interaction with GPIb-IX, platelet lysates were incubated with beads conjugated with recombinant 14-3-3-maltose-binding protein (MBP) fusion protein in the absence or presence of MPαC or control peptides. GPIb-IX from platelet lysates specifically bound to 14-3-3 beads but not the control MBP-conjugated beads (FIG. 1B). The binding of GPIb-IX to 14-3-3 beads was abolished by the MPαC peptide but not the non-phosphorylated identical peptide or scrambled peptide, indicating that MPαC specifically interfere with 14-3-3 binding to GPIb-IX (FIG. 1B).

The MPαC and control peptides were then preincubated with platelet-rich plasma to determine their effect on platelet function. MPαC dose-dependently inhibited vWF-dependent platelet aggregation induced by ristocetin (a vWF modulator that mimics the effect of subendothelium to induce vWF-GPIb interaction) (FIG. 1C). In contrast, myristoylated control peptides, MαC or MαCsc, had no significant effect (FIG. 1D). Similarly, myristic anhydride (MA) also had no effect on ristocetin-induced platelet aggregation (FIG. 1E), suggesting that myristoylation is not responsible for the inhibitory effect of the peptide. On the other hand, a non-myristoylated phospho-peptide identical to MPαC (PαC) had no effect on ristocetin-induced platelet aggregation (FIG. 1E), suggesting that myristoylation is required for the inhibitory effect. Thus, these data indicate that the inhibitory effect of MPαC requires membrane permeability of this specific 14-3-3 binding peptide.

Ristocetin-induced platelet aggregation involves platelet agglutination that is caused by the cross-linking of platelets by GPIb-IX-bound vWF, platelet activation and subsequent integrin αIIbβ3-mediated platelet aggregation. To differentiate if the inhibitory effect of MPαC result from inhibition of platelet agglutination induced by vWF binding or GPIb-IX-mediated platelet activation, the effect of MPαC on ristocetin-induced platelet agglutination was examined in the presence of RGDS peptide, which blocks integrin-dependent platelet aggregation. MPαC completely inhibited ristocetin-induced platelet agglutination in the presence of RGDS (FIG. 2A, 2B). In contrast, control peptides had no inhibitory effect. Also, MPαC inhibited botrocetin-induced platelet agglutination. Furthermore, to exclude the possibility that MPαC may affect general platelet activation process, the effect of this peptide on platelet aggregation induced by platelet agonists ADP, collagen, and thromboxane A2 analog U46619 was examined.

MPαC as well as control peptides had no inhibitory effect on platelet aggregation induced by these agonists (FIGS. 2C, 2D and 2E). Thus the effect of MPαC peptide is specific for GPIb-IX-dependent platelet agglutination. To directly verify if MPαC affected vWF binding, the inventors examined if MPαC affected ristocetin-induced vWF binding to GPIb-IX (to exclude the possible role of integrin in vWF binding, binding assays were performed in the presence of 10 mM EDTA or RGDS; SEQ ID NO:7). MPαC inhibited ristocetin-induced vWF binding to platelets (FIG. 3). In contrast, the control peptides had no inhibitory effect. These data indicate that a cell-permeable peptide that blocks 14-3-3 binding to GPIbα cytoplasmic domain specifically inhibits vWF binding to the extracellular ligand binding domain of GPIb-IX. Thus, 14-3-3 binding to the C-terminal region of GPIbα is required for maintaining vWF binding function of GPIb-IX in platelets.

Physiological function of vWF binding to GPIb-IX is to mediate platelet adhesion under flow conditions. Thus, if 14-3-3 interaction with GPIb-IX is important for the physiological function of GPIb-IX, MPαC peptide should inhibit platelet adhesion to vWF under flow conditions. To investigate the effect of MPαC on platelets adhesion under flow, washed platelets were preincubated with peptides or vehicle (DMSO) control, then perfused into vWF-coated glass capillaries. To exclude the role of integrins, these experiments were performed in the presence of integrin inhibitor, RGDS (SEQ ID NO:7). As expected, platelets preincubated with vehicle or control peptides adhered on vWF surface. In contrast, there was almost no adhesion of platelets preincubated with MPαC (FIG. 4A). The dramatic effect of MPαC peptide to inhibit platelet adhesion not only indicates that 14-3-3 interaction with the cytoplasmic domain of GPIbα is important to platelet adhesion function, but also suggests that MPαC or similar peptides that block 14-3-3 binding to GPIbα can be used as a new class of anti-platelet agents that specifically inhibit GPIb-IX-dependent platelet adhesion.

To explore the possibility whether MPαC can be used as an anti-platelet agent in vivo, and to examine the role of 14-3-3 binding to GPIb-IX in in vivo platelet function, MPαC or control peptides MαC and MαCsc were infused into the jugular vein of anesthetized C57B mice in a double-blinded fashion. After allowing the peptides to circulate for 5 minutes, tail bleeding time analysis, which is a widely used assay for in vivo hemostatic function in mice (Offermanns et al., Nature, 389:183-186 (1997); Ware et al., Proc. Natl. Acad. Sci. USA, 97:2803-2808 (2000); Sambrano et al., Nature, 413:74-78. (2001) Li et al., Cell, 112:77-86 (2003)), were performed to these mice. Median bleeding time was significantly prolonged in mice treated with MPαC as compared with mice injected with MαC or MαCsc (p<0.0001) (FIG. 4B). These data demonstrate that 14-3-3 binding to GPIb-IX cytoplasmic domain is important for in vivo hemostatic function of platelets, and MPαC peptide indeed has anti-thrombotic effect in vivo.

The above data indicate that 14-3-3 binding to the cytoplasmic domain of GPIbα is required for GPIb-IX to maintain an active state capable of binding vWF. Phosphorylation-dependent binding sites for the dimeric 14-3-3 are present in the cytoplasmic domains of both GPIbα and GPIbβ (FIG. 1A). A binding site in GPIbα resides in the C-terminal SIRYSGHpS$^{609}$L (SEQ ID NO:1) sequence in which Ser$^{609}$ is constitutively phosphorylated in resting platelets (Bodnar et al., J. Biol. Chem., 274:33474-33479 (1999)). The binding site in GPIbβ is located in the RLpS$^{166}$LTDP sequence (Andrews et al., Biochemistry, 37:638-647 (1998); Calverley et al., Blood, 91:1295-1303 (1998)) in which Ser$^{166}$ can be phosphorylated by cAMP-dependent protein kinase (PKA) upon activation by elevated intracellular cAMP (Wardell et al., J. Biol. Chem., 264:15656-15661 (1989)). However, binding of 14-3-3 to GPIbα does not require cooperation of the 14-3-3 binding site in GPIbβ (Gu et al., J. Biol. Chem., 273:33465-33471 (1998)). On the other hand, deletion of the binding site in GPIbα abolishes high affinity binding of 14-3-3 to GPIb-IX, suggesting that GPIbβ alone is not sufficient to support high affinity binding of 14-3-35. These data suggest that GPIb-IX should normally have two different 14-3-3 interacting modes (FIG. 4C): (1) 14-3-3 dimer binds to both GPIbα and GPIβ sites when PKA is activated by elevated cAMP; and (2) 14-3-3 dimer binds only to GPIbα but not GPIbβ when cAMP level is low. PKA-mediated phosphorylation of GPIbβ inhibits vWF binding function of GPIb-IX and that dephosphorylation of GPIbβ is associated with activation of vWF binding function of GPIb-IX (Bodnar et al., J. Biol. Chem., 277:47080-47087 (2002)). Thus, the data described in this example further suggest a new model of GPIb-IX regulation. In this model, elevation of cAMP induces binding of 14-3-3 to both sites in GPIbα and GPIbβ resulting in a "resting" GPIb-IX. Decreases in cAMP level dissociate GPIbβ-14-3-3 interaction, resulting in the binding of 14-3-3 to GPIbα alone and activating vWF binding function of GPIb-IX, which can be inhibited by disrupting 14-3-3-binding to GPIbα (FIG. 4C). Therefore, 14-3-3 is a regulator of vWF binding function of GPIb-IX and is required for the activation of the receptor function of GPIb-IX.

GPIb-IX, as a major platelet adhesion receptor, is an excellent target for anti-thrombosis drug development. Due to the critical roles GPIb-IX plays in platelet adhesion under high shear rate flow conditions, GPIb-IX-specific inhibitors are likely to have selective effects for arterial thrombosis (for example, in stenotic arteries) or micro-thrombosis (for example, in arterioles and capillaries). In addition, in patients suffering from thrombotic thrombocytopenic purpura and other types of thrombotic microangiopathy, micro-thrombosis can be directly induced by the spontaneous interaction between circulating vWF and GPIb-IX (Moake, Annu. Rev. Med., 53:75-88 (2002)). Thus, development of a GPIb-IX-specific anti-platelet drug will be useful in treating these types thrombotic diseases. Here it is demonstrated that pharmacological blockade of the interaction between 14-3-3 and GPIbα with MPαC inhibits vWF binding function of GPIb-IX and platelet adhesion, and reduces in vivo hemostatic function. Thus, MPαC or similar reagents that block GPIb-IX-14-3-3 interaction are potentially useful as a new class of anti-thrombotic agents.

Example 4

Additional Studies Relating to Background of the Anti-Platelet Peptides

Protein kinase A (PKA)-dependent phosphorylation of platelet glycoprotein (GP) Ibβ at $Ser^{166}$ negatively regulates von Willebrand factor (VWF) binding function of the glycoprotein Ib-IX complex (GPIb-IX). Thus, GPIb-IX containing a mutant GPIbβ replacing $Ser^{166}$ with alanine ($S^{166}A$) showed enhanced VWF binding when expressed in Chinese hamster ovary (CHO) cells. However, when this GPIbβ mutant was complexed with a GPIbα mutant in which $Ser^{609}$, a key residue required for high affinity 14-3-3 binding, was substituted by alanine ($S^{609}A$), the enhancing effect of $S^{166}A$ mutation on vWF binding was diminished. Similarly, a PKA inhibitor, which causes GPIbβ dephosphorylation, enhanced vWF binding to wild type GPIb-IX. This effect, however, was reduced in cells expressing $S^{609}A$ mutant of GPIbα complexed with wild type GPIbβ, indicating that the interaction between 14-3-3 and GPIbα C-terminal domain is required for the enhancement of vWF binding induced by GPIbβ dephosphorylation. Furthermore, enhanced vWF binding function in $S^{166}A$ cells was associated with an increased GPIb-IX dissociation from the membrane skeleton, and this effect was also reduced by $S^{609}A$ mutation. These data suggest a novel regulatory mechanism of GPIb-IX in which intracellular signals regulates GPIb-IX association with the membrane skeleton and ligand binding function of GPIb-IX in a 14-3-3-dependent manner. The following example experimental details and results that led to these findings.

Materials and Methods

Reagents—Monoclonal antibody WM23 against GPIbα, monoclonal antibodies SZ29, against vWF, and SZ2, against GPIbα, and monoclonal antibody against GPIb-IX, P3, were obtained from sources known to those of skill in the art (Berndt et al., Eur. J. Biochem., 151(3):637-649 (1985); Ruan et al., Blood, 69(2):570-577 (1987); Ruan et al., Chung Hua Nei Ko Tsa Chih, 25(9):547-550, 576, (1986)). cDNA clones encoding wild type GPIbα, GPIbβ, and GPIX were obtained from sources known to those of skill in the art (Lopez et al., Proc. Natl. Acad. Sci. USA, 84(16):5615-5619 (1987); Lopez et al., Proc. Natl. Acad. Sci. USA, 85(7):2135-2139 (1988)). Bovine serum albumin (BSA), aprotinin, ristocetin, and dimethyl sulfoxide (DMSO) were purchased from Sigma (St. Louis, Mo.). Non-essential amino acids, penicillin and streptomycin, and L-glutamine were purchased from Life Technologies Inc. (Carlsbad, Calif.). The membrane permeable PKA inhibitor, myristoylated PKI was purchased from Calbiochem (San Diego, Calif.). The calpain inhibitor E64 was purchased from Roche Molecular Biochemicals (Indianapolis, Ind.). Goat anti-mouse immunoglobulin (IgG) conjugated with horseradish peroxidase (HRP), FITC-conjugated goat anti-mouse IgG were purchased from Biosource (Camarillo, Calif.).

Recombinant GPIb-IX and mutants—CHO cells expressing recombinant wild type GPIb-IX, a GPIb-IX mutant with a serine to alanine point mutation at Ser166 in GPIbβ ($S^{166}A$), and GPIb-IX mutants with truncations at 591 and 605 in the cytoplasmic domain of GPIbα were described previously (Bodnar et al., J. Biol. Chem., 277(49):47080-47087 (2002); Du et al., J. Biol. Chem., 271:7362-7367 (1996)). Site directed mutagenesis that replaces Ser 609 of GPIbα to an alanine (S609A) was performed using PCR method with the forward primer as AGAAGAATTCGCTGCTCTGACCACA (SEQ ID NO:5) and the reverse primer as TAAGTCTAGAT-CAGAGGGCGTGGCCAGAGT (SEQ ID NO:6). The PCR product was cloned into TA vector (Invitrogen), and inserted into wild type GPIbα in pGEM3Z(+) vector after digestion with restriction enzymes Sma I and BamH I. The resulting S609A mutant were then subcloned into pCDNA3.1(−) vector after digestion with EcoR I. Correct mutation was verified by DNA sequencing. Transfection of cDNA into CHO cells was performed using LipofectAMINE Plus (Invitrogen) as recommended by the manufacturer. Stable cell lines were selected using selection media containing 0.5 mg/ml G418 and further selected by cell sorting using the anti-GPIbα monoclonal antibody, SZ2. Expression of GPIb-IX in different cell lines was adjusted by cell sorting to comparable levels before experiments.

Flow Cytometric Analysis of VWF Binding to GPIb-IX-expressing Cells—CHO cells expressing wild type (1b9) and mutant GPIb-IX were grown to confluence to synchronize cell growth. The cells were detached using 0.5 mM EDTA in PBS, pH 7.4. Seventy-five percent of the original volume was then replated in Dulbecco's modified Eagle's medium (DMEM) growth media and cultured for 18 h. For VWF binding assays, cells were detached using 0.5 mM EDTA-PBS, pH 7.4, resuspended to a concentration of $2.25 \times 10^6$ cells/ml and incubated in modified Tyrode's buffer (2.5 mM Hepes, 12.1 mM $NaHCO_3$, 2.36 mM KCl, 0.136 M NaCl, 1 mM $CaCl_2$, 1 mM $MgCl_2$, 0.1% D-glucose, 1% BSA, pH 7.4) for 30 min at 4° C. Ristocetin (1.25 mg/ml) and purified vWF (35 µg/ml) were added to cell suspension and incubated at 22° C. for 30 min. After washing once with Tyrode's buffer, cells were further incubated with 10 µg/ml FITC-labeled SZ-29 (a monoclonal antibody against vWF) in the dark at 22° C. for 30 min and then analyzed by flow cytometry. In some experiments, VWF were preincubated with FITC-labelled SZ29 and then allowed to incubate with cells for 30 min.

The cells were then analyzed by flow cytometry without washing. Results obtained with these two different VWF binding methods were very similar. As negative controls, cells were incubated with ristocetin in the absence of VWF. To examine the effects of myristoylated PKI, cells were preincubated with or without 200 µM PKI for 15 min at 22° C., prior to analysis for VWF binding.

Cell Adhesion under Flow—Purified human vWF was diluted to a final concentration of 30 µg/ml with 0.1 mM NaHCO3, pH 8.3, and coated onto glass capillary tubes (inner diameter 0.58 mm, Harvard Apparatus Inc.) overnight in a humid environment at 4° C. The cover capillaries were washed with PBS to remove unbound vWF, blocked with 5% BSA in PBS at room temperature for 2 hrs, and then installed on the stage of an inverted microscope. The cells were suspended in modified Tyrode's buffer containing 0.5% BSA ($5×10^6$ cells/mL), and then perfused by a syringe pump (PhD, Harvard Apparatus Inc.) into the glass capillaries at various shear rates for 2.5 min. Shear rate was calculated as described by Slack and Turitto (Slack et al., Thromb. Haemost., 72(5): 777-781 (1994)). Transient adhesion (rolling) of cells on the vWF-coated surface was recorded on video cassette recorder, and the rolling cells were counted in 10 randomly selected fields and at randomly selected time points.

Coimmunoprecipitation of GPIb-IX with 14-3-3—CHO cells expressing wild type and mutant GPIb-IX were resuspended in Hepes buffer (137 mM NaCl, 2.7 mM KCl, 1 mM $MgCl_2$, 5.6 mM D-glucose, 3.3 mM $Na_2HPO_4$, 3.8 mM Hepes, pH 7.35) to a concentration of $1.0×10^8$ cells/ml then solubilized by adding an equal volume of solubilization buffer (0.1 M Tris, 0.01 M EGTA, 0.15 M NaCl, and 2% Triton X-100, pH 7.4) containing 0.2 mM E64 and 1 mM phenylmethylsulfonyl fluoride (PMSF), 1 mM DTT, and 0.08 U/mL aprotinin. The samples were centrifuged at 100,000×g at 4° C. for 30 min to remove the Triton X-100 insoluble material. Cell lysate (150 µl) was incubated with anti-GPIbα monoclonal antibody P3 for 1 hour, and then with protein G-conjugated Sepharose 4Bbeads for 1 hour at 4° C. The beads were then washed three times with 1:1 mix of Hepes buffer and lysis buffer. Bound proteins were extracted by the addition of SDS-sample buffer and immunoblotted with an anti-14-3-3% antibody (Gu et al., J. Biol. Chem., 273(50): 33465-33471 (1998)).

Association of GPIb-IX with Triton X-100-insoluble membrane skeleton—CHO cells expressing wild type or mutant GPIb-IX were resuspended in Tyrode's buffer with 0.1% BSA to a concentration of $1.0×10^7$ cells/ml. The cells were incubated at 4° C. for 30 min, then solubilized in an equal volume of lysis buffer containing 0.2 mM E64, 2 mM PMSF, and 0.08 U/ml aprotinin for 30 min at 4° C. The lysate was centrifuged at 2000×g for 5 min to remove the nuclei. The cell lysates were then centrifuged at 100,000×g for 3 hours at 4° C. The insoluble pellet and supernatant were dissolved in identical final volumes of SDS-sample buffer containing 5% β-mercaptoethanol, and then Western blotted for GPIbα using the monoclonal antibody, MW23.

Results

There are two known phosphorylation sites in the cytoplasmic domain of GPIb-IX. Ser609 in the vast majority of GPIbα molecules is constitutively phosphorylated in platelets (Bodnar et al., J. Biol. Chem., 274(47):33474-33479 (1999)). Phosphorylation at this site is required for high affinity binding of 14-3-3 to the C-terminal domain of GPIbα. Ser166 of GPIbβ is phosphorylated by cAMP-dependent protein kinase (PKA), an event dynamically regulated by intracellular cAMP level (Fox et al., J. Biol. Chem., 262(26):12627-12631 (1987); Fox et al., J. Biol. Chem., 264(16):9520-9526 (1989)). Phosphorylation at Ser166 is important in 14-3-3 interaction with the cytoplasmic domain of GPIbβ (Andrews et al., Biochemistry, 37(2):638-647 (1998); Calverley et al., Blood, 91(4):1295-1303 (1998); Feng et al., Blood, 95(2): 551-557 (2000)). PKA-dependent phosphorylation at Ser166 of GPIbβ negatively regulates vWF binding function of GPIb-IX (Bodnar et al., J. Biol. Chem., 277(49):47080-47087 (2002)). Thus, dephosphorylation of Ser166 enhances vWF binding function of GPIb-IX. To further investigate the roles of serine phopshorylation in regulating GPIb-IX function, cell lines were established that express following mutants of GPIb-IX: (1) GPIb-IX with wild type GPIbβ and GPIX complexed with a GPIbα-mutant bearing a conserved mutation of Ser609 to an alanine residue (S609A), (2) GPIb-IX with wild type GPIbα and GPIX complexed with a mutant of GPIbβ in which Ser166 is mutated to an alanine (S166A), and (3) GPIb-IX bearing both GPIbα S609A and GPIbβ S166A mutations (S166A/S609A). By repeated cell sorting using anti-GPIb monoclonal antibodies, cells lines with expression levels of these different mutants comparable to a wild type GPIb-IX cell line (1b9) were obtained.

To determine the roles of the above described two phosphoserine residues in regulating ligand binding function of GPIb-IX, CHO cell lines bearing wild type and the mutants of GPIb-IX were incubated with purified VWF in the presence of ristocetin (a VWF modulator that induces VWF binding to GPIb-IX). Binding of VWF was determined by flow cytometry using an anti-VWF monoclonal antibody. As reported previously (Englund et al., J. Biol. Chem., 276(20):16952-16959 (2001); Bodnar et al., J. Biol. Chem., 277(49):47080-47087 (2002)), only a low level of VWF binding to wild type GPIb-IX expressed in CHO cells (1b9) was detected. This is because GPIb-IX molecules expressed in CHO cells are phosphorylated at Ser166 and thus in a "resting" form (Bodnar et al., J. Biol. Chem., 277(49):47080-47087 (2002)). In contrast, vWF binding to cells expressing S166A mutant was significantly higher, indicating that this mutant has an enhanced vWF binding function. GPIbα S609A mutation by itself has no significant effect on vWF binding function as indicated by similar levels of VWF binding compared to wild type GPIb-IX expressing cells. However, when S609A mutant of GPIbα were complexed with S166A mutant of GPIbβ, the enhancing effect of S166A on VWF binding was diminished. Thus, the phosphoserine 609 is required for the enhancing effects of S166A mutation on vWF binding function.

GPIb-IX binding to vWF mediates transient adhesion (or rolling) of platelets on the subendothelial-bound vWF under flow conditions. Therefore, studies were performed to determine whether Ser609 mutation in the GPIbα C-terminal 14-3-3 binding also affect GPIb-IX-dependent cell adhesion to vWF under flow conditions. It was seen that a very low number of CHO cells expressing wild type GPIb-IX (1b9) were able to adhere and roll on vWF-coated surface at a shear rate of 250 s−1. In contrast, the S166A mutant cells showed a significantly enhanced adhesion. This enhancing effect of S166A mutation was diminished in S166A/S609A cells, indicating that the phosphoserine 609 is required in S166A mutation-induced activation of cell adhesion mediated by GPIb-IX.

The S166A mutation of GPIbβ is highly conserved because the only difference between serine and alanine is the presence of a hydroxyl group, which serves as the phosphorylation site. Since Ser166 of wild type GPIbβ expressed in CHO cells is known to be phosphorylated, it is likely that the effects of S166A mutant on enhancing vWF binding function of GPIb-IX result from abrogation of Ser166 phosphorylation. Therefore, the data that GPIbα S609A mutation abolishes the enhancement of vWF binding function by S166A mutation suggest the possibility that GPIbα phosphoserine 609 is required for Ser166-dephosphorylation induced upregulation of vWF binding function of GPIb-IX. A specific membrane permeable PKA inhibitor, the myristoylated PKA inhibitor peptide (PKI), has been shown to cause dephosphorylation of GPIbβ Ser166 and thus enhances VWF binding function of GPIb-IX (Bodnar et al., J. Biol. Chem., 277(49): 47080-47087 (2002)). Thus, the inventors further examined whether the S609A mutation of GPIbα could also reverse the enhancing effect of PKI on vWF binding to GPIb-IX. To do this, cells expressing wild type or S609A mutant of GPIb-IX were preincubated with PKI and then examined for ristocetin-induced vWF binding. Previously, it has been shown that PKI treatment significantly reduced phosphorylation at Ser166 of GPIbβ, but has no significant effect on GPIbα Ser609 phosphorylation (Bodnar et al., J. Biol. Chem., 277(49):47080-47087 (2002); Bodnar et al., J. Biol. Chem., 274(47):33474-33479 (1999)). PKI treatment significantly enhanced vWF binding to wild type GPIb-IX (1b9 cells), but this effect was dramatically reduced in the S609A mutant. This result indicates that phosphoserine 609 is important in Ser166-dephosphorylation-induced enhancement of vWF binding to GPIb-IX.

Phosphoserine 609 is a key residue in the high affinity binding of 14-3-3 to GPIbα. Thus, the effect of S609A mutation is likely to result from a loss of 14-3-3 binding. To determine if deletion of entire 14-3-3 binding site in the C-terminal domain of GPIbα would also have effects similar to S609A, the effects of PKI on vWF binding function of two different mutants of GPIb-IX, Δ591 and Δ605, lacking the GPIbα C-terminal 20 and 5 residues respectively was examined. PKI-induced upregulation of vWF binding was inhibited in Δ591 and Δ605 mutants, suggesting that the 14-3-3 binding region in the C-terminus of GPIbα is important in the GPIbβ phosphorylation (dephosphorylation)-induced dynamic regulation of VWF binding function of GPIb-IX.

Both Phosphoserine 609 of GPIbα and phosphoserine 166 of GPIbβ have been shown to be the key residues in 14-3-3 binding sites. Thus, it is likely that the effects of S166A and S609A mutants on VWF binding function of GPIb-IX result from loss of 14-3-3 binding to GPIbα and GPIbβ respectively. To determine whether these mutants affect endogenous 14-3-3 binding to GPIb-IX, 1b9, S609A, S166A and S609A/S609A cells were solubilized and immunoprecipitated with an anti-GPIbα antibody. The immunoprecipitates were then immunoblotted with an anti-14-3-3 antibody.

The results showed that 14-3-3 co-immunoprecipitated with wild type GPIb-IX and also with S166A mutant, suggesting that S166A mutation is not sufficient to reduce 14-3-3 binding. In contrast, 14-3-3 failed to co-immunoprecipitate with S609A mutant or S609A/S166A mutants. Thus, although there are 3 different 14-3-3 binding sites in the cytoplasmic domain of GPIb-IX complex, the site containing the phosphoserine 609 is required for high affinity interaction between GPIb-IX and endogenous 14-3-3 under these conditions. These data also suggest that the 14-3-3 binding site in the cytoplasmic domain of GPIbβ, by itself, is not sufficient to support the high affinity interaction between GPIb-IX and 14-3-3. Hence, anchoring of 14-3-3 to the C-terminal domain of GPIbα may facilitate the potential interaction between the dimeric 14-3-3 with GPIbβ or other sites in the cytoplasmic domains of GPIb-IX.

It is known that the cytoplasmic domain of GPIbβ interacts with filamin and thus links GPIb-IX to short actin filamental structure underlying the membrane, which is referred to as "the membrane skeleton". The association of GPIb-IX with the membrane skeleton negatively regulates VWF binding function of GPIb-IX. The present example demonstrates that disruption of Ser166 phosphorylation enhances VWF binding to GPIb-IX by a mechanism that requires 14-3-3 binding site in the C-terminal domain of GPIbα. To determine the relationship between these two seemingly different regulatory mechanisms of VWF-GPIb-IX interaction, the association of wild type and different mutants of GPIb-IX with the membrane skeleton were examined. These studies showed that the majority of wild type GPIb-IX molecules is associated with Triton X-100 insoluble membrane skeleton fraction that can be sedimented at 100,000 g. In contrast, there is a significant fraction of S166A mutant present in the soluble fraction. When GPIbβ S166A mutant is complexed with GPIbα S609A mutant (S166A/S609A), soluble fraction was reduced compared with S166A mutant. These data suggest that dephosphorylation of GPIbβ at Ser166 made GPIb-IX more likely to dissociate from the membrane skeleton, which was shown to enhance the vWF binding function of GPIb-IX. Taken together, these data suggest that phosphorylation of Ser609 of GPIbα and phosphorylation-dependent binding of 14-3-3 to the C-terminal site of GPIbα is required for Ser166-dephosphorylation-induced dissociation of GPIb-IX from the membrane skeleton and subsequent upregulation of VWF binding function of GPIb-IX.

Discussion

In the present example, it is shown that the key residue in GPIbα C-terminal 14-3-3 binding site, phosphoserine609, is required in upregulating vWF binding function of GPIb-IX induced by dephosphorylation of Ser166, and is also required for GPIbβ dephosphorylation-induced regulation of GPIb-IX association with the membrane skeleton.

The results that phosphorylation of GPIbβ Ser166 and GPIbα Ser609 regulates ligand binding function of GPIb-IX suggest a role for the phosphoserine-dependent signaling molecule, 14-3-3, in regulating ligand binding function of GPIb-IX. Among the identified 14-3-3 binding sites, only the GPIbβ interaction with 14-3-3 is known to be dynamically regulated by PKA-dependent phosphorylation at Ser166 (Wardell et al., J. Biol. Chem., 264(26):15656-15661 (1989)). Thus, the data that phosphorylation at Ser166 down regulates vWF binding to GPIb-IX suggests that interaction between 14-3-3 and GPIbβ, which is enhanced by Ser166 phosphorylation, negatively regulates ligand binding function of GPIb-IX. Conversely, dephosphorylation of Ser166 appears to upregulate VWF binding by disruption of 14-3-3 binding to GPIbβ. Furthermore, these data suggest that upregulation of vWF binding function induced by Ser166 dephosphorylation requires phosphorylation-dependent binding of 14-3-3 to GPIbα C-terminal binding site, because disruption of the C-terminal 14-3-3 binding site in GPIbα reversed the Ser166 dephosphorylation-induced upregulation of VWF binding. Thus these results suggest that intracellular signals, by controlling PKA activity, regulate ligand binding function of GPIb-IX by modulating 14-3-3 binding states of GPIb-IX.

The 14-3-3 protein is dimeric. Each monomer of the 14-3-3 dimer has a binding pocket, and thus the dimeric 14-3-3 is able to simultaneously interact with two different sites of a protein or two different ligands (Liu et al., Nature, 376(6536): 191-194 (1995); Xiao et al., Nature, 376(6536):188-191 (1995); Braselmann et al., EMBO J. 14(19):4839-4848 (1995)). Therefore, it is possible that different 14-3-3 binding sites in GPIb-IX may interact with the single 14-3-3 dimer. It has previously shown that high affinity binding of 14-3-3 to GPIb-IX requires GPIbα C-terminal 14-3-3 binding site (Bodnar et al., J. Biol. Chem., 274(47):33474-33479 (1999)), in which the constitutively phosphorylated Ser609 plays a key role. It has also been shown that binding of monomeric 14-3-3 to GPIb-IX is significantly lower than dimeric 14-3-3, suggesting that high affinity binding of dimeric 14-3-3 to GPIb-IX involves simultaneous interaction with two 14-3-3 binding sites (Gu et al., J. Biol. Chem., 273(50):33465-33471 (1998)). PKA-dependent phosphorylation of Ser166 forms a high affinity 14-3-3 binding site in GPIbβ. Thus it is likely that a 14-3-3 dimer can interact with both GPIbα C-terminal and GPIbβ 14-3-3 binding sites when GPIbβ is phosphorylated at Ser166. Conversely, dephosphorylation of GPIbβ

Ser166 reduces 14-3-3 affinity for GPIbβ under which conditions 14-3-3 only interact with the GPIbα cytoplasmic domain. This interaction is required for the upregulation of vWF binding function induced by Ser166 dephosphorylation. Thus, while there are alternative possibilities, current data suggest that PKA-mediated switch between a 14-3-3 dimer binding to both GPIbα and GPIbβ and 14-3-3 binding to GPIbα alone determines whether GPIb-IX is in a "resting" state, or an "active" state. Therefore, the inventors propose a "toggle switch" model as a possible regulatory mechanism of GPIb-IX function. As discussed above, simultaneous occupation of two binding sites in GPIb-IX cytoplasmic domain are important in high affinity binding of 14-3-3, and one of the binding site must be the GPIbα C-terminal RYSGHpS609L sequence. While PKA-phosphorylated GPIbβ can serve as the other binding site, deletion of GPIbβ 14-3-3 binding site or S166A mutation do not reduce 14-3-3 binding to GPIb-IX, suggesting that, when 14-3-3 binding site in GPIbβ is disrupted, 14-3-3 may still interact with two 14-3-3 binding sites. Since there is evidence indicating the presence of a second 14-3-3 binding site in the central region of GPIbα cytoplasmic domain (Andrews et al., Biochemistry, 37(2): 638-647 (1998); Feng et al., Blood, 95(2):551-557 (2000)), it is possible that a 14-3-3 dimer simultaneously interact with two binding sites in GPIbα when GPIbβ is dephosphorylated, which switches on the ligand binding function of GPIb-IX. PKA-mediated phosphorylation of GPIbβ allows high affinity interaction of 14-3-3 with both GPIbα and GPIbβ, switching off ligand binding function.

Interestingly, the second binding site for 14-3-3 in the central region of GPIbα overlaps with filamin binding site (Andrews et al., J. Biol. Chem., 267(26):18605-18611 (1992); Andrews et al., Biochemistry, 37(2):638-647 (1998); Feng et al., Blood, 102(6):2122-2129 (2003)), suggesting a possibility that 14-3-3 interaction with this region of GPIbα may interfere with GPIb-IX association with the membrane skeleton. This possibility is supported by data that disruption of Ser166 phosphorylation site by S166A mutation decreases percentage of GPIb-IX molecules that are associated with the Triton X-100-insoluble membrane skeleton, and that the effect of S166A mutation on GPIb-IX association with the membrane skeleton is significantly attenuated by disruption of the C-terminal 14-3-3 binding site in GPIbα. Thus, it is possible that the 14-3-3 "toggle switch" regulates GPIb-IX association with the membrane skeleton actin filaments. Since previous studies show that dissociation of GPIb-IX with the membrane skeleton enhances VWF binding function (Englund et al., J. Biol. Chem., 276(20):16952-16959 (2001)), it is possible that the 14-3-3 "toggle switch", by controlling the association of GPIb-IX with the membrane skeleton, regulates vWF binding function of GPIb-IX.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A composition comprising a myristoylated peptide having an amino acid sequence of:
   a. SIRYSGHpSL (SEQ ID NO: 29),
   b. a fragment of SEQ ID NO: 29 that retains a 14-3-3 binding activity, wherein the fragment is SEQ ID NO: 10, or
   c. a conservative variant of SEQ ID NO: 29 that retains a 14-3-3 binding activity, wherein the variant is SEQ ID NO: 8 or SEQ ID NO: 9,
   wherein the peptide comprises a myristoyl group at the C-terminus, or at the N-terminus of the peptide, optionally comprising a pharmaceutically acceptable carrier, diluent or excipient.

2. The composition of claim 1, wherein said peptide is phosphorylated.

3. The composition of claim 1, wherein said peptide is between about 10 amino acids and about 50 amino acids in length.

4. The composition of claim 1, wherein said peptide inhibits the binding of von Willebrands factor to blood platelets, or other cells that express GPIb-IX, and/or inhibits GPIb-IX dependent platelet aggregation.

5. The composition of claim 1, further comprising an additional agent selected from the group consisting of a fibrinolytic molecule, an anticoagulant and an anti-platelet agent.

6. The composition of claim 5, wherein said anticoagulant is selected from the group consisting of a heparin, hirudin or activated protein C.

7. The composition of claim 5, wherein said fibrinolytic molecule is plasmin or a plasminogen activator.

8. The composition of claim 7, wherein said plasminogen activator is selected from the group consisting of staphylokinase, streptokinase, prourokinase, urokinase, tissue-type plasminogen activator and vampire bat plasminogen activator.

9. The composition of claim 1, further comprising a heparin composition, wherein said heparin composition is a low molecular weight heparin composition.

10. The composition of claim 9, wherein said a low molecular weight heparin composition is selected from the group consisting of tinzaparin, certoparin, parnaparin, nadroparin, ardeparin, enoxaparin, reviparin, reviparin, dalteparin, and fraxiparin.

11. The composition of claim 5, wherein said an anti-platelet agent is selected from the group consisting of ticlopidinem aspirin, clopidrigel or an inhibitor of glycoprotein IIb/IIIa function.

12. The composition of claim 5, wherein said an anti-platelet agent is selected from the group consisting of Aggrastat™, Aggrenox™, Agrylin™, Flolan™, Integrilin™, Presantine™, Plavix™, Pletal™ and REoPro™.

* * * * *